(12) United States Patent
Markel

(10) Patent No.: US 9,131,892 B2
(45) Date of Patent: Sep. 15, 2015

(54) WEARABLE ITEMS PROVIDING PHYSIOLOGICAL, ENVIRONMENTAL AND SITUATIONAL PARAMETER MONITORING

(76) Inventor: Gal Markel, Haifa (IL)

( * ) Notice: Subject to any disclaimer, the term of this patent is extended or adjusted under 35 U.S.C. 154(b) by 199 days.

(21) Appl. No.: 12/955,495

(22) Filed: Nov. 29, 2010

(65) Prior Publication Data

US 2012/0136231 A1    May 31, 2012

(51) Int. Cl.
- A61B 5/04 (2006.01)
- A61B 5/00 (2006.01)
- A61B 5/0408 (2006.01)
- A61B 5/02 (2006.01)

(52) U.S. Cl.
CPC ............. *A61B 5/6805* (2013.01); *A61B 5/0015* (2013.01); *A61B 5/04085* (2013.01); *A61B 5/0024* (2013.01)

(58) Field of Classification Search
CPC ............. A61B 5/0205; A61B 5/02055; A61B 5/1118; A61B 2560/0242; A61B 5/0402; A61B 5/0452; A61B 5/0008; A61B 5/6804; A61B 5/6805
USPC ......... 600/372, 382, 384, 386, 388–391, 393, 600/508–509, 513
See application file for complete search history.

(56) References Cited

U.S. PATENT DOCUMENTS

| | | | |
|---|---|---|---|
| 4,889,131 A * | 12/1989 | Salem et al. ................. | 600/484 |
| 5,465,727 A | 11/1995 | Reinhold, Jr. | |
| 6,047,203 A | 4/2000 | Sackner | |
| 6,073,046 A | 6/2000 | Patel et al. | |
| 6,219,408 B1 | 4/2001 | Kurth | |
| 6,264,614 B1 | 7/2001 | Albert et al. | |
| 6,381,482 B1 | 4/2002 | Jayaraman et al. | |
| 6,485,416 B1 | 11/2002 | Platt et al. | |
| 7,117,031 B2 | 10/2006 | Lohman et al. | |
| 2003/0140060 A1* | 7/2003 | Gehlot et al. .............. | 707/104.1 |
| 2003/0212319 A1 | 11/2003 | Magill | |
| 2005/0239493 A1 | 10/2005 | Batkin et al. | |
| 2005/0245839 A1* | 11/2005 | Stivoric et al. ................ | 600/549 |
| 2006/0125623 A1* | 6/2006 | Appelt et al. ................. | 340/521 |
| 2006/0142654 A1 | 6/2006 | Rytky | |
| 2006/0264730 A1* | 11/2006 | Stivoric et al. ................ | 600/390 |
| 2007/0021677 A1 | 1/2007 | Markel | |
| 2007/0078324 A1* | 4/2007 | Wijisiriwardana ........... | 600/386 |
| 2008/0287770 A1* | 11/2008 | Kurzweil et al. ............. | 600/388 |
| 2009/0088652 A1 | 4/2009 | Tremblay | |
| 2009/0227876 A1* | 9/2009 | Tran .............................. | 600/483 |
| 2010/0049006 A1 | 2/2010 | Magar | |
| 2010/0082302 A1 | 4/2010 | Garudadri | |

OTHER PUBLICATIONS

PCT, Notification of Transmittal of the International Search Report and the Written Opinion of the International Searching Authority, in International application PCT/IL11/00898, dated Apr. 19, 2012.
PCT, Notification Concerning Transmittal of International Preliminary Report on Patentability, in application No. PCT/IL2011/000898, dated Jun. 13, 2013 (7 pages).
Supplementary Partial European Search Report for EP 11845912 dated Jun. 30, 2015 (5 pages).

* cited by examiner

*Primary Examiner* — Joseph Stoklosa
*Assistant Examiner* — Brian M Antiskay
(74) *Attorney, Agent, or Firm* — McAndrews, Held & Malloy, Ltd.

(57) ABSTRACT

A garment and/or garment system with health-monitoring (e.g., cardiovascular monitoring) capability, substantially as shown in and/or described in connection with at least one of the figures, as set forth more completely in the claims.

51 Claims, 18 Drawing Sheets

WEARABLE ITEMS PROVIDING PHYSIOLOGICAL, ENVIRONMENTAL AND SITUATIONAL PARAMETER MONITORING

CROSS-REFERENCE TO RELATED APPLICATIONS/INCORPORATION BY REFERENCE

This application is related to U.S. patent application Ser. No. 11/492,278, filed Jul. 25, 2006, and titled "Mobile Communication Device and Other Devices with Cardiovascular Monitoring Capability", the contents of which are hereby incorporated herein in their entirety by reference.

FEDERALLY SPONSORED RESEARCH OR DEVELOPMENT

[Not Applicable]

SEQUENCE LISTING

[Not Applicable]

MICROFICHE/COPYRIGHT REFERENCE

[Not Applicable]

BACKGROUND OF THE INVENTION

A substantial portion of cardiovascular and other health-related problems exhibit detectable symptoms. In various scenarios where an individual is being monitored, medical assistance may be obtained based on monitored physiological characteristics before a particular health issue becomes fatal.

Present cardiovascular and other types of health monitoring systems are cumbersome and inconvenient (e.g., impractical for everyday use). Additionally, in many fatal incidents (e.g., incidents involving various cardiovascular pathologies), the individual had no prior knowledge of serious health issues that would have caused the individual to seek medical assistance and possibly obtain dedicated health monitoring (e.g. heart monitoring) apparatus. Further, in many health-monitoring scenarios, physiological characteristics are monitored and analyzed out of context, leading to misdiagnosis.

Further limitations and disadvantages of conventional and traditional approaches will become apparent to one of skill in the art, through comparison of such systems with the present invention as set forth in the remainder of the present application with reference to the drawings.

BRIEF SUMMARY OF THE INVENTION

Various aspects of the present invention provide a garment and/or garment system with health-monitoring (e.g., cardiovascular monitoring) capability. These and other advantages, aspects and novel features of the present invention, as well as details of illustrative aspects thereof, will be more fully understood from the following description and drawings.

DETAILED DESCRIPTION OF THE INVENTION

Figure 1:
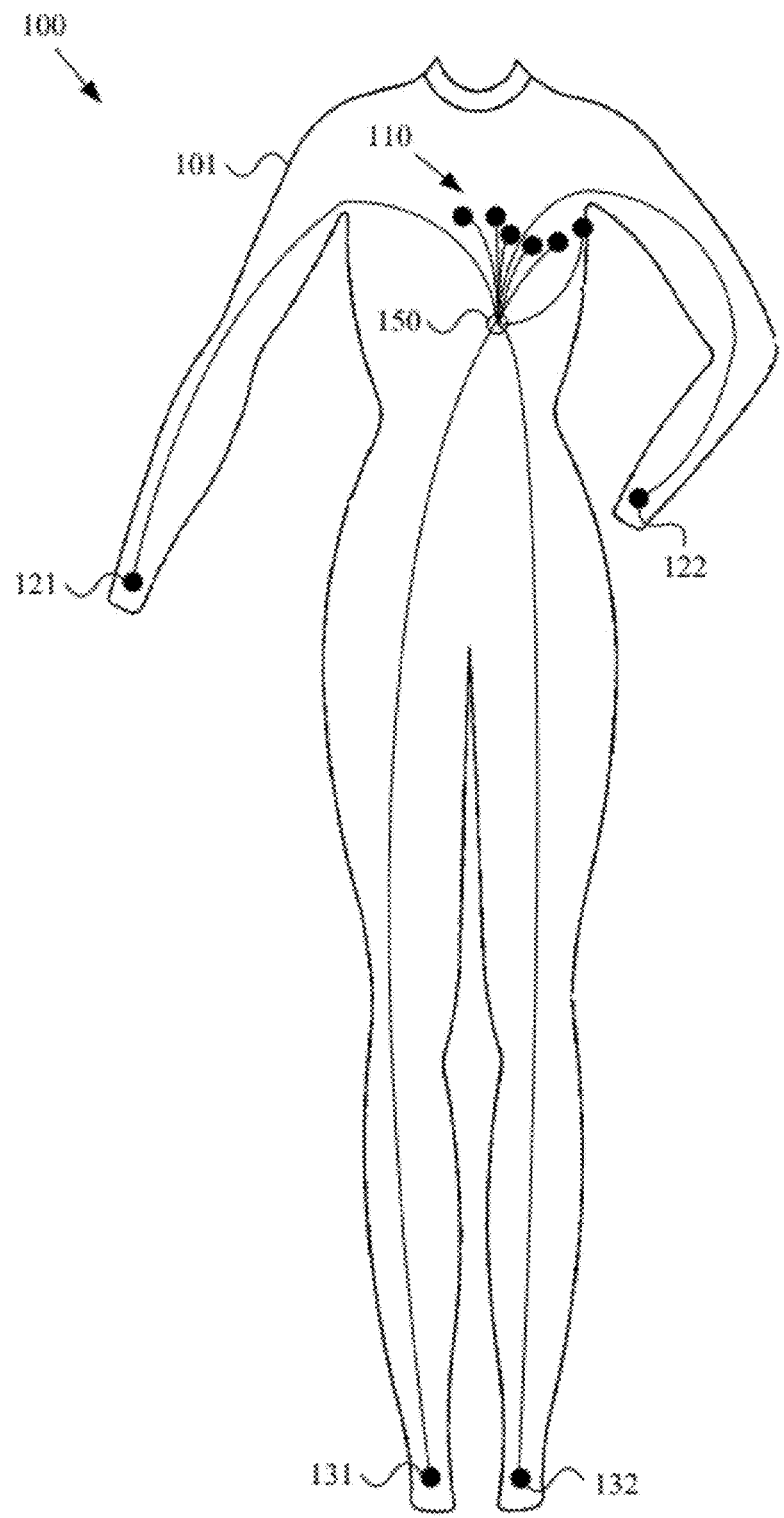
FIG. 1 is a diagram illustrating an exemplary garment (e.g., full body suit) health-monitoring system, in accordance with various aspects of the present invention.

Various aspects of the present invention may, for example, include and/or utilize various sensors that are integrated into one or more garments. Such garments may, for example, generally correspond to articles of clothing that a person may wear throughout the course of typical life activities (e.g., sleeping, eating, walking, working, exercising, watching television, doing household chores, traveling, socializing, etc.). Such garments do not necessarily need to be health-care specific garments (e.g., a hospital gown, a specific garment worn in a hospital in a control environment for a specific test, etc.). For example and without limitation, such garments may comprise: a full or partial body suit, a long-sleeve shirt, short-sleeve shirt, sleeveless shirt, pants, shorts, socks, swimwear, a sports bra, undergarments, a wet suit, thermal wear, a glove, and so on. Various aspects of the present invention may also apply to protective gear, for example, as may be worn during performing hazardous jobs (e.g., a hard hat, body armor, etc.), participating in risky recreational, sporting, law enforcement, or military activities, etc. (e.g., a ball glove, hockey glove, a helmet, sports padding, male/female protective gear, joint braces, flak jacket or ballistic vest, eyewear, etc.).

The integrated sensors may comprise and/or comprise characteristics of any of a variety of different types of sensors, signals from which may be analyzed to ascertain health. Such sensors may, for example, comprise physiological sensors that operate to monitor physiological characteristics of a person (or subject). Such physiological sensors may, for example and without limitation, comprise: heart monitoring sensors (e.g., heart-rate monitoring sensors, electrocardiogram (ECG or EKG) sensors), body temperature sensors, breath-rate/respiration sensors (e.g., pressure-based (e.g., material stress, air pressure/bladder, etc.), acoustic-based, etc.), skin conductivity sensors, oxygen saturation sensors, blood perfusion sensors, etc.).

Such sensors may also, for example, comprise non-physiological sensors that operate to monitor characteristics other than physiological characteristics of the subject. Such non-physiological sensors may, for example, comprise environmental sensors that operate to monitor aspects of the environment in which a subject is performing a task. For example and without limitation, such environmental sensors may comprise: air temperature sensors, air speed sensors, humidity sensors, air oxygen level sensors, barometric pressure sensors, altitude/elevation sensors, precipitation sensors, light sensors, location sensors/systems (e.g., global positioning system (GPS) sensors, terrestrial triangulation sensors/systems (e.g., cellular communication system based, premises based, campus based, etc.)), time sensors (e.g., time change and/or absolute time), orientation sensors, etc.

Such non-physiological sensors may also, for example, comprise situational sensors that operate to monitor characteristics of a physical situation (e.g., a task or activity) in which the subject is engaged. Such situation (or activity) sensors may, for example and without limitation, comprise: weight sensors, impact sensors, force sensors, pressure sensors, accelerometers, inclinometers, motion sensors, speed and/or velocity sensors, etc.

The manner in which the various sensors are incorporated into a garment depend on the nature of the particular sensors. For example, a sensor (or portions thereof) may be attached to a garment after the bare garment is manufactured. In an exemplary scenario, a sensor may be snapped, adhered and/or sewn to an already completed garment. In such scenario, portions of a sensor that need (or prefer) direct contact with the subject skin may be secured to the inside of the garment. For example, a conductive button may be positioned to contact the skin of the subject, conductive fibers and/or protrusions may be sewn into the garment to contact the skin of the subject, etc. Also, in such a scenario, portions of a sensor that need not contact the subject's skin may be positioned away from the skin to reduce irritation. Further, in such a scenario, a general-sized garment may be utilized, while sensor placement may be customized to a particular subject (e.g., as opposed to custom garment production for a particular subject). Such a scenario provides flexibility for positioning particular placement-sensitive sensors (e.g., at least some ECG sensors) at locations suited for a particular subject (or user).

In other exemplary scenarios, particular sensors (or portions thereof) may be formed into the garment while the garment is being formed. In such a scenario, conductive pads and/or fibers may be incorporated into the garment during manufacture of the garment. In various scenarios in which location of the sensor need not be precise (e.g., a skin temperature sensor, location sensor, etc.), such sensors may be incorporated into the garment during manufacture in a one-size-fits-all or one-size-fits-many design. In such a scenario, location-critical sensors may be added later for a particular subject.

In another exemplary scenario, the specifications for a garment and sensor placement may be customized for a particular subject, and such specifications may then be provided to a manufacturer of the garment for customized production of the garment.

In still another exemplary scenario, a form-fitting garment may be produced that comprises a generic matrix of conductive regions that contact the skin of the subject. Such conductive regions may, for example, be formed by alternating fabric regions of conductive and non-conductive material. As a non-limiting example, an entire garment may be formed of non-conductive material and then conductive fibers may be woven into the fabric to create the matrix of conductive regions. In such a scenario, an optimum set of conductive regions may then be selected after production (e.g., by a health-care professional), and such conductive regions may then be utilized as skin contact points for selected sensors and/or conductively connected to form conductive pathways in the garment.

Various garment sensors may, for example, be self-contained sensors comprising their own respective power supply and their own respective communication circuitry. Such sensors may, for example, operate to wirelessly communicate sensor information to a processor. In such a scenario, a conductive coupling need not be incorporated into the garment for such sensor.

Various other garment sensors, however, may require and/or prefer utilization of conductive paths (e.g., for power supply, for measuring electrical characteristics between two points, for communicating information, for reducing signal noise relative to wireless RF communication, etc.). For such sensors, leads (e.g., wire leads, conductive fiber leads, etc.) may be woven into the garment, run via garment seams, etc. As a non-limiting example, various portions of the following discussion may include discussion of ECG sensors (or contacts) incorporated into a garment. Since ECG analysis includes analyzing differences in electrical potential between various skin contact points (or electrodes), connections to such skin contact points may be formed in the garment for convenient access In general, conductive paths may be formed into the garment (e.g., utilizing conductive fiber) to assist in measuring such differences in electrical potential.

Various garment sensors may, for example, require (or prefer) consistent and firm conductive contact with the subject's skin. For example, such operation is characteristic of ECG electrodes. For such sensors (or electrodes), the garment (e.g., in addition to being form-fitting or in lieu of being form-fitting) may comprise regions of extra elasticity formed to enhance the stability and contact of such sensors with the subject's skin. As a non-limiting example, six electrodes for a 12-lead ECG run across the chest of the subject. One or more regions of extra elasticity may be formed in the garment to ensure that each of such sensors adequately contacts and remains in contact with the chest of the user. Similarly, the limb electrodes of the 12-lead ECG may be secured by the incorporation of respective regions of extra elasticity in a garment (e.g., an arm/wrist band, a leg/ankle band, etc.).

Additionally, various garment sensors may be shaped, positioned or formed in any of a variety of manners, depending on the nature of the particular sensor. For example, some sensor surfaces (e.g., electrodes) may generally comprise conductive material. For example, an electrode may comprise a metallic surface exposed for user contact. Also for example, an electrode may be formed from conductive plastic (or another material) that may be integrated into various molded components of the mobile communication device. For example, various conductive plastics (e.g., graphite-impregnated plastic or the like) may provide sufficient conductivity for an electrode to perform adequately. It should be recognized that the scope of various aspects of the present invention should not be limited by characteristics of particular electrodes or electrode placements unless explicitly claimed.

Electrodes (or other sensors) may be shaped, positioned or formed with various physical features to enhance collection of cardiovascular information from a user. For example and without limitation, an electrode may comprise one or more projections to enhance conductive contact with a user. Also, an electrode may comprise one or more depressions or indentations to enhance conductive contact with a user.

Electrodes may also be identified for the user in any of a variety of manners or may be generally concealed from the user. For example, an electrode may comprise a visible or tactile indicium to indicate the location of the electrode to a user. Alternatively, a sensor may be integrated into a garment in a manner that is generally unnoticeable to a wearer of the garment.

The following discussions of FIGS. 1-11 will now provide various non-limiting examples of garment/sensor configurations. It should be noted that such examples are for illustrative purposes only and are not meant to be limiting. Accordingly, the scope of various aspects of the present invention should not be limited by characteristics of any of such examples unless explicitly claimed.

FIG. 1 is a diagram illustrating an exemplary garment (e.g., comprising a full body suit) health-monitoring system 100, in accordance with various aspects of the present invention. The exemplary system 100 comprises a garment 101. The garment 101 comprises characteristics of a full-body suit (e.g., which may or may not comprise gloves, socks and a hood).

The garment comprises a plurality of ECG sensors (or electrodes) integrated with the garment 101. For example, the garment 101 comprises ten sensors (or electrodes) disposed at locations generally associated with a twelve-lead ECG. Such sensors comprise a series of six chest (or torso) sensors 110. Such chest sensors 110 may, for example, comprise a $V_1$ sensor (or electrode) disposed in the fourth intercostal space (between ribs 4 and 5) just to the right of the sternum of a subject when the garment 101 is worn by the subject, a $V_2$ sensor disposed in the fourth intercostal space (between ribs 4 and 5) just to the left of the sternum of a subject when the garment 101 is worn by the subject, a $V_3$ sensor disposed between sensors $V_2$ and $V_4$, a $V_4$ sensor disposed in the fifth intercostal space between ribs 5 and 6) in the mid-clavicular line of a subject when the garment 101 is worn by the subject, a $V_5$ sensor disposed horizontally even with the $V_4$ sensor and in the anterior axillary line of a subject when the garment 101 is worn by the subject, and a $V_6$ sensor disposed horizontally even with $V_4$ and $V_5$ in the midaxillary line of a subject when the garment 101 is worn by the subject. As discussed above, the ECG sensors (or electrodes) are positioned in the garment 101 at such locations and the garment is formed in such a manner (e.g., with the appropriate form-fitting elasticity) that conductive electrodes are generally in constant contact with the skin of the subject wearing the garment 101.

The garment 101 also comprises a plurality of ECG limb sensors. For example, the garment 101 comprises a RA electrode 121 disposed on the right arm of the garment 101 (e.g., near the right wrist) and a LA electrode 122 disposed on the left arm of the garment 101 (e.g., near the left wrist). Also for example, the garment 101 comprises a RL electrode 131 on the right leg of the garment 101 (e.g., near the right ankle) and a LL electrode 132 disposed on the left leg of the garment 101 (e.g., near the left ankle).

Each of the ECG electrodes 110, 121, 122, 131 and 132 are conductively coupled (e.g., utilizing conductive fiber and/or wire) to a central location 150 on the garment 101 at which the respective electrodes may each be conveniently accessed (e.g., individually and/or in aggregate) by measurement and/or processing circuitry. For example, ECG analysis comprises measuring differences in electrical potential between various electrodes. Note that sensors (e.g., electrodes or others) may also be incorporated into the back of the garment. For example, dorsal ECG sensors may be added as desired.

In an exemplary scenario, the central location 150 may comprise a communication hub by which measurement circuitry may electrically access the electrodes. In another exemplary scenario, circuitry that operates to measure such electrical potential may be disposed on the garment 101 at the central location 150. Such circuitry may then, for example, operate to communicate information of such measurements to other circuitry (e.g., also disposed at the central location 150, disposed elsewhere on the garment, or located off-garment) for analysis and/or communication to other circuitry.

In an additional exemplary scenario, circuitry that operates to measure such electrical potential may be disposed on the garment 101 at the central location 150. Circuitry that operates to analyze such ECG measurement results and produce ECG data may also be disposed on the garment 101 at the central location 150. Such analysis circuitry may then, for example, operate to communicate information of such measurements to other circuitry (e.g., also disposed at the central location 150, disposed elsewhere on the garment, or located off-garment) for analysis and/or communication to other circuitry.

In yet another exemplary scenario, circuitry that operates to measure such electrical potential may be disposed on the garment 101 at the central location 150. Circuitry that operates to analyze such ECG measurement results and produce ECG data may also be disposed on the garment 101 at the central location 150. Circuitry that operates to analyze the ECG data (e.g., in a manner discussed later with regard to FIGS. 12-14) may also be disposed on the garment 101 at the central location 150 or at another location. For example, any or all components (or modules) of the system 1500 illustrated at FIG. 15 may be so disposed. Additionally, central location 150 may also, for example, comprise a power supply (e.g., a battery) or be conductively coupled to a power supply (e.g., a power supply integrated into the garment 101 and/or off-garment).

Figure 2:
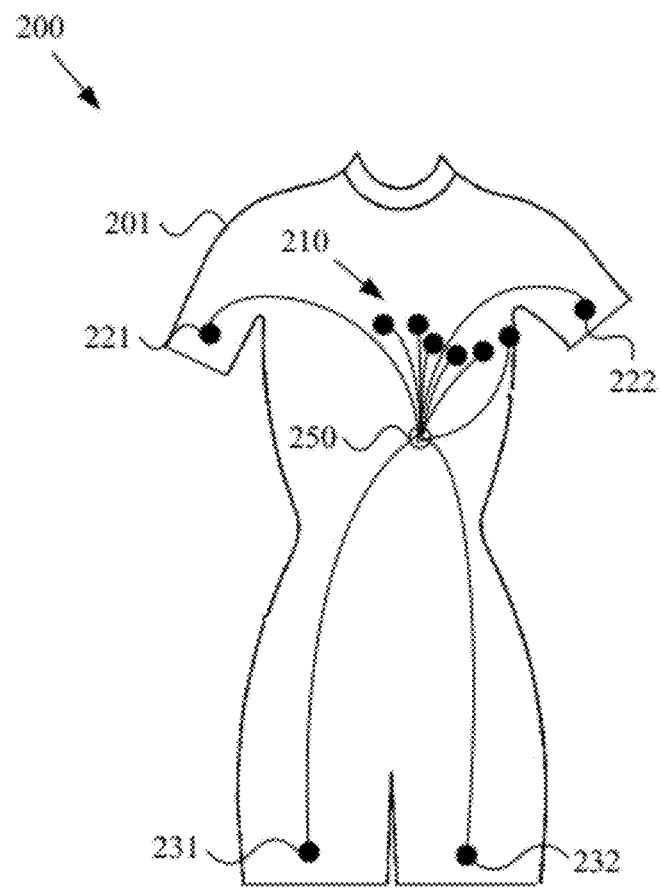
FIG. 2 is a diagram illustrating an exemplary garment (e.g., partial body suit) health-monitoring system, in accordance with various aspects of the present invention.

FIG. 2 is a diagram illustrating an exemplary garment (e.g., comprising a partial body suit) health-monitoring system 200, in accordance with various aspects of the present invention. The system 200 may, for example, share any or all characteristics of the exemplary system 100 illustrated at FIG. 1 and discussed previously.

The exemplary system 200 comprises a garment 201. The garment 201 comprises a plurality of ECG sensors (or electrodes) integrated into the garment 201. For example, the garment 201 comprises ten sensors (or electrodes) disposed at locations generally associated with a twelve-lead ECG. Such sensors comprise a series of six chest (or torso) sensors 210. Such chest sensors 210 may, for example, be disposed on the garment 201 in the same manner as discussed with regard to the chest sensors 110 and the garment 101 of FIG. 1.

The garment 201 also comprises a plurality of ECG limb sensors. For example, the garment 201 comprises a RA electrode 221 disposed on the right arm of the garment 201 (e.g., on the right upper arm) and a LA electrode 222 disposed on the left arm of the garment 201 (e.g., on the left upper arm). Also for example, the garment 201 comprises a RL electrode 231 on the right leg of the garment 201 (e.g., near the right thigh) and a LL electrode 232 disposed on the left leg of the garment 201 (e.g., near the left thigh).

Each of the ECG electrodes 210, 221, 222, 231 and 232 are conductively coupled (e.g., utilizing conductive fiber and/or wire) to a central location 250 on the garment 201 at which the respective electrodes may each be conveniently accessed by measurement and/or processing circuitry. As discussed with regard to the central location 150 of the garment 101 of FIG. 1, the central location 250 may comprise a communication hub by which measurement circuitry may electrically access the electrodes, communication circuitry that operates to communicate ECG measurement signals and/or data to other circuitry, analysis circuitry to analyze ECG measurement data and/or communication circuitry to communicate with other circuitry regarding analysis results. The central location 250 may also, for example, comprise a power supply (e.g., a battery) and/or a conductive coupling to a power supply.

Figure 3:
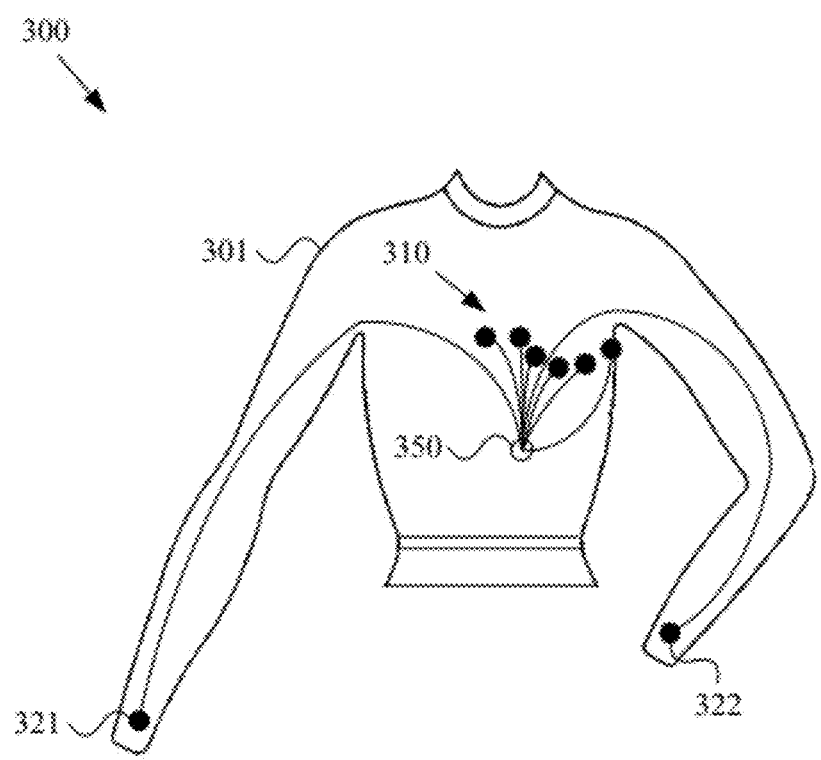
FIG. 3 is a diagram illustrating an exemplary garment (e.g., shirt) health-monitoring system, in accordance with various aspects of the present invention.

FIG. 3 is a diagram illustrating an exemplary garment (e.g., shirt) health-monitoring system 300, in accordance with various aspects of the present invention. The system 300 may, for example, share any or all characteristics of the exemplary systems 100 and 200 illustrated at FIGS. 1-2 and discussed previously.

The exemplary system 300 comprises a garment 301. The garment 301 comprises a plurality of ECG sensors (or electrodes) integrated into the garment 301. For example, the garment 301 comprises eight sensors (or electrodes) disposed at locations generally associated with a twelve-lead ECG minus the two leg sensors. Such sensors comprise a series of six chest (or torso) sensors 310. Such chest sensors 310 may, for example, be disposed on the garment 301 in the same manner as discussed with regard to the chest sensors 110 and garment 101 of FIG. 1.

The garment 301 also comprises a plurality of ECG limb sensors. For example, the garment 301 comprises a RA electrode 321 disposed on the right arm of the garment 301 (e.g., near the right wrist) and a LA electrode 322 disposed on the left arm of the garment 301 (e.g., near the left wrist). As discussed above, the garment 301 does not include ECG leg sensors. As such, external ECG leg sensors may be utilized for a complete 12-lead ECG analysis, or a less-than-12-lead ECG analysis may be performed utilizing just the electrodes of the garment 301.

Each of the ECG electrodes 310, 321 and 322 are conductively coupled (e.g., utilizing conductive fiber and/or wire) to a central location 350 on the garment 301 at which the respective electrodes may each be conveniently accessed by measurement and/or processing circuitry. As discussed with regard to the central location 150 of the garment 101 of FIG. 1, the central location 350 may comprise a communication hub by which measurement circuitry may electrically access the electrodes, communication circuitry that operates to communicate ECG measurement signals and/or data to other circuitry, analysis circuitry to analyze ECG measurement data and/or communication circuitry to communicate with other circuitry regarding analysis results. The central location 350 may also, for example, comprise a power supply (e.g., a battery) and/or a conductive coupling to a power supply.

Figure 4:
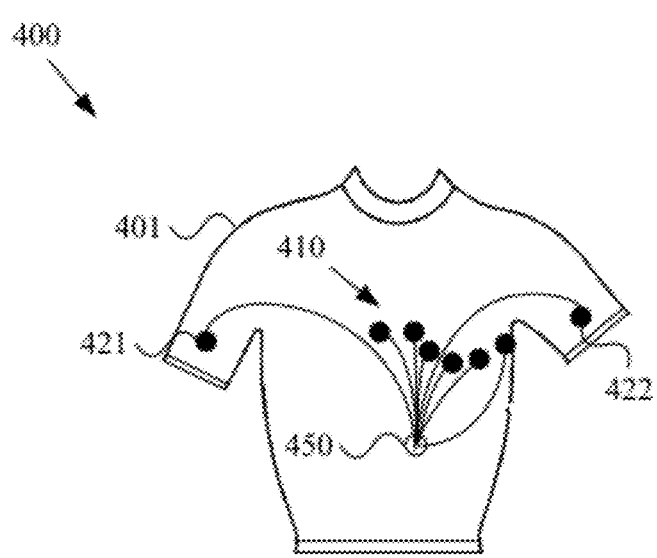
FIG. 4 is a diagram illustrating an exemplary garment (e.g., short-sleeve shirt) health-monitoring system, in accordance with various aspects of the present invention.

FIG. 4 is a diagram illustrating an exemplary garment (e.g., short-sleeve shirt) health-monitoring system 400, in accordance with various aspects of the present invention. The system 400 may, for example, share any or all characteristics of the exemplary systems 100, 200 and 300 illustrated at FIGS. 1-3 and discussed previously.

The exemplary system 400 comprises a garment 401. The garment 401 comprises a plurality of ECG sensors (or electrodes) integrated into the garment 401. For example, the garment 401 comprises eight sensors (or electrodes) disposed at locations generally associated with a twelve-lead ECG minus the two leg sensors. Such sensors comprise a series of six chest (or torso) sensors 410. Such chest sensors 410 may, for example, be disposed on the garment 401 in the same manner as discussed with regard to the chest sensors 110 and garment 101 of FIG. 1.

The garment 401 also comprises a plurality of ECG limb sensors. For example, the garment 401 comprises a RA electrode 421 disposed on the right arm of the garment 201 (e.g., at the right upper arm) and a LA electrode 422 disposed on the left arm of the garment 201 (e.g., at the left upper arm). As discussed above, the garment 401 does not include ECG leg sensors. As such, external ECG leg sensors may be utilized for a complete 12-lead ECG analysis, or a less-than-12-lead ECG analysis may be performed utilizing just sensors of the garment 401.

Each of the ECG electrodes 410, 421 and 422 are conductively coupled (e.g., utilizing conductive fiber and/or wire) to a central location 450 on the garment 401 at which the respective electrodes may each be conveniently accessed by measurement and/or processing circuitry. As discussed with regard to the central location 150 of the garment 101 of FIG. 1, the central location 450 may comprise a communication hub by which measurement circuitry may electrically access the electrodes, communication circuitry that operates to communicate ECG measurement signals and/or data to other circuitry, analysis circuitry to analyze ECG measurement data and/or communication circuitry to communicate with other circuitry regarding analysis results. The central location 450 may also, for example, comprise a power supply (e.g., a battery) or a conductive coupling to a power supply.

Figure 5:
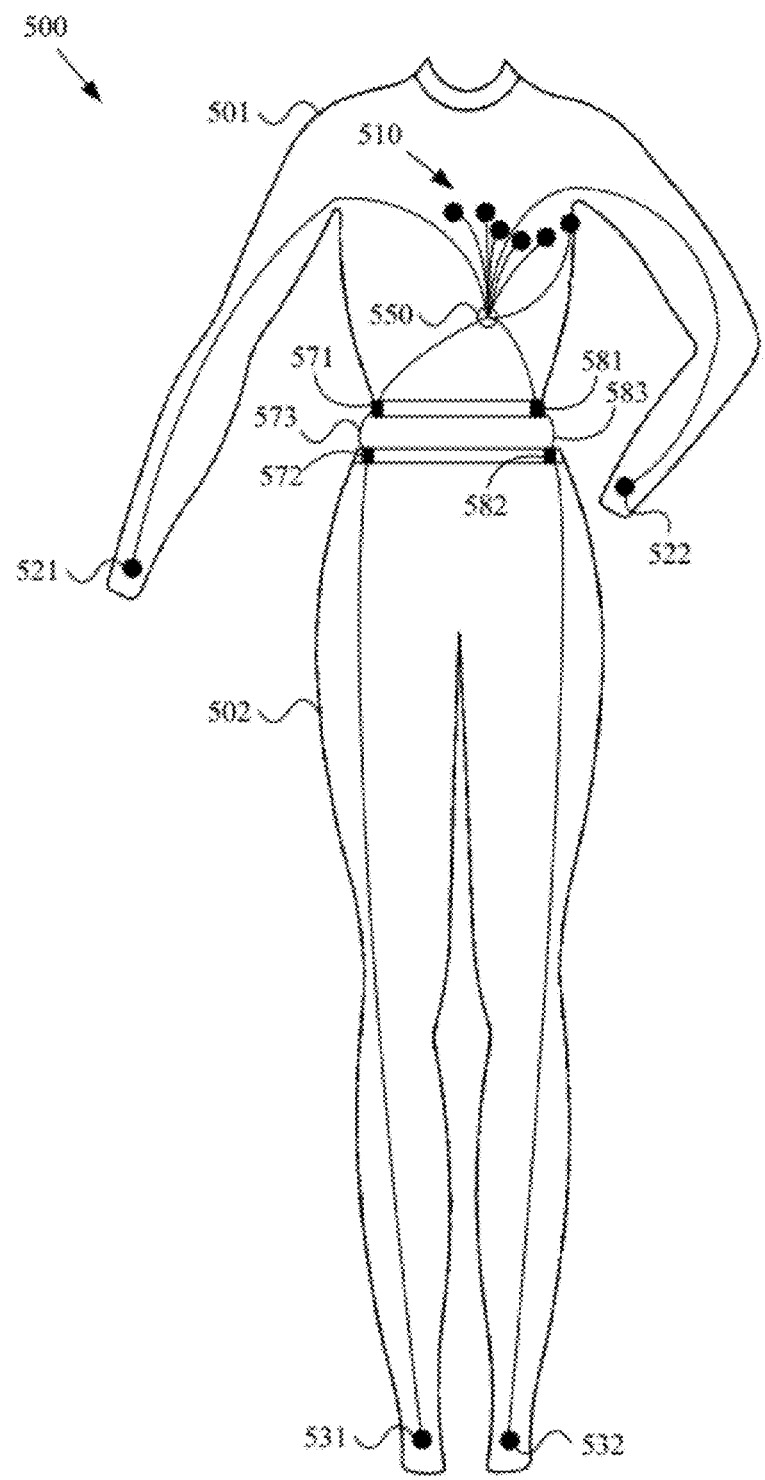
FIG. 5 is a diagram illustrating an exemplary garment (e.g., shirt and pants) health-monitoring system, in accordance with various aspects of the present invention.

FIG. 5 is a diagram illustrating an exemplary garment (e.g., shirt and pants) health-monitoring system 500, in accordance with various aspects of the present invention. The system 500 may, for example, share any or all characteristics of the exemplary systems 100, 200, 300 and 400 illustrated at FIGS. 1-4 and discussed previously.

The exemplary system 500 comprises a first garment 501 and a second garment 502. The first garment 501 and the second garment 502 each comprise a respective plurality of ECG sensors (or electrodes) integrated into such garments. For example, the first garment 501 comprises eight sensors (or electrodes) disposed at locations generally associated with a twelve-lead ECG minus the two leg sensors. Such sensors comprise a series of six chest (or torso) sensors 510. Such chest sensors 510 may, for example, be disposed on the first garment 501 in the same manner as discussed with regard to the chest sensors 110 and garment 101 of FIG. 1.

The first garment 501 also comprises a plurality of ECG limb sensors. For example, the first garment 501 comprises a RA electrode 521 disposed on the right arm of the first garment 501 (e.g., near the right wrist) and a LA electrode 522 disposed on the left arm of the first garment 501 (e.g., near the left wrist). The first garment 501 does not include ECG leg sensors. As such, external ECG leg sensors may be utilized for a complete 12-lead ECG analysis, or a less-than-12-lead ECG analysis may be performed utilizing only the ECG sensors of the first garment 501. The second garment 502, however, comprises the two ECG leg sensors integrated with the second garment 502. For example, the second garment 502 comprises a RL electrode 531 disposed on the right leg of the second garment 502 (e.g., near the right ankle) and a LL electrode 532 disposed on the left leg of the second garment 502 (e.g., near the left leg).

Each of the ECG electrodes 510, 521 and 522 on the first garment 501 are conductively coupled (e.g., utilizing conductive fiber and/or wire) to a central location 550 on the first garment 501 at which the respective electrodes may each be conveniently accessed by measurement and/or processing circuitry. Additionally, each of the leg electrodes 531 and 532 on the second garment 501 are also conductively coupled to the central location 550 on the first garment 501 at which the respective electrodes may each be conveniently accessed by measurement and/or processing circuitry. For example, first garment 501 comprises an upper right terminal 571 and an upper left terminal 581 that are conductively coupled to the central location 550 on the first garment 501, and the second garment 502 comprises a lower right terminal 572 that is conductively coupled to the LL electrode 532 and a lower left terminal 582 that is conductively coupled to the RL electrode 532. A right conductive link 573 conductively couples the upper right terminal 571 and lower right terminal 572 thereby conductively coupling the RL electrode 531 to the central location 550, and a left conductive link 583 conductively couples the upper left terminal 581 and the lower left terminal 582 thereby conductively coupling the LL electrode 532 to the central location 550. The conductive links 573 and 583 may be formed in any of a variety of manners (e.g., via metal clips and conductors, via Velcro and conductive plastics, etc.).

As discussed with regard to the central location 150 of the garment 101 of FIG. 1, the central location 550 may comprise a communication hub by which measurement circuitry may electrically access the individual electrodes, communication circuitry that operates to communicate ECG measurement signals and/or data to other circuitry, analysis circuitry to analyze ECG measurement data and/or communication circuitry to communicate with other circuitry regarding analysis results. The central location 550 may also, for example, comprise a power supply (e.g., a battery) and/or a conductive coupling to a power supply.

The previous discussion of FIGS. 1-5 focused on ECG sensors (or electrodes) and the communication and/or processing associated therewith. Such focus on ECG sensors was for illustrative purposes only. As such, the scope of various aspects of the present invention should not be limited to ECG sensors, communicating and/or processing unless explicitly claimed. For example, the scope of various aspects of the present invention applies equally well to any of a variety of different types of sensors (e.g., individually and/or in combination with other types of sensors). The following discussion of FIGS. 6-11 will provide non-limiting examples of various sensor combinations. For example, a garment based health-monitoring system may utilize any of a large variety of different types of sensors (e.g., combinations of different types of physiological sensors, combinations of physiological sensors, environmental sensors and/or situational sensors, etc.). Non-limiting examples of such different types of sensors were provided above.

Figure 6:
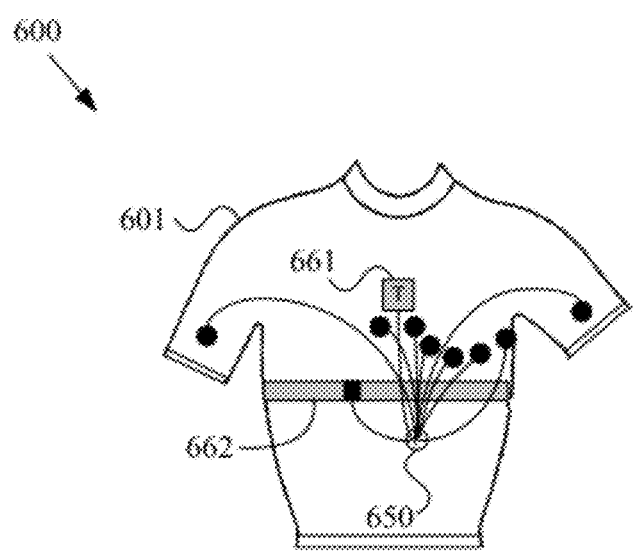
FIG. 6 is a diagram illustrating an exemplary garment (e.g., short-sleeve shirt) health-monitoring system, in accordance with various aspects of the present invention.

FIG. 6 is a diagram illustrating an exemplary garment (e.g., short-sleeve shirt) health-monitoring system 600, in accordance with various aspects of the present invention. The system 600 may, for example, share any or all characteristics of the exemplary systems 100, 200, 300, 400 and 500 illustrated at FIGS. 1-5 and discussed previously.

The exemplary system 600 comprises a garment 601. The garment 601 comprises a plurality of ECG sensors (or electrodes) integrated into the garment 601. For example, the garment 601 comprises eight sensors (or electrodes) disposed at locations generally associated with a twelve-lead ECG minus the two leg sensors. Such sensors comprise a series of six chest (or torso) sensors and two arm sensors as discussed with the exemplary garment 401 illustrated in FIG. 4.

The garment 601 also comprises other sensors in addition to ECG sensors. For example, the garment 601 comprises a body temperature sensor 661 that operates to measure the body temperature of a wearer of the garment 601. Though the body temperature sensor 661 is illustrated on the chest of the garment 601 for illustrative clarity, such sensor 661 may be positioned anywhere on the garment 601 or off the garment 601, depending on the type of body temperature monitoring desired. The body temperature sensor 661 may be communicatively coupled to the central location 650 of the garment 601 (e.g., for communication and/or electrical power).

The garment 601 additionally comprises a breath rate (or respiration rate) sensor 662. The breath rate sensor 662 operates to measure the breath rate (or respiration rate) of a wearer of the garment 601. Such a sensor 662 may, for example and without limitation, be based on mechanical stress, air bladder pressure, acoustic monitoring, etc.). Though the breath rate sensor 662 is illustrated as a chest band of the garment 601 for illustrative clarity, such sensor 662 may be positioned anywhere on the garment 601 (e.g., near the throat, at the abdomen, etc.) or off the garment 601, depending on the type of respiration monitoring desired. The breath rate sensor 662 may be communicatively coupled to the central location 650 of the garment 601 (e.g., for communication and/or electrical power).

Figure 7:
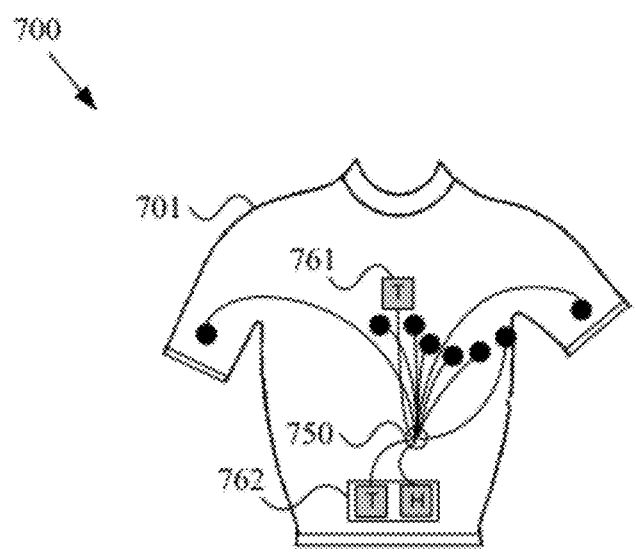
FIG. 7 is a diagram illustrating an exemplary garment (e.g., short-sleeve shirt) health-monitoring system, in accordance with various aspects of the present invention.

FIG. 7 is a diagram illustrating an exemplary garment (e.g., short-sleeve shirt) health-monitoring system 700, in accordance with various aspects of the present invention. The system 700 may, for example, share any or all characteristics of the exemplary systems 100, 200, 300, 400, 500 and 600 illustrated at FIGS. 1-6 and discussed previously.

The exemplary system 700 comprises a garment 701. The garment 701 comprises a plurality of ECG sensors (or electrodes) integrated into the garment 701. For example, the garment 701 comprises eight sensors (or electrodes) disposed at locations generally associated with a twelve-lead ECG minus the two leg sensors. Such sensors comprise a series of six chest (or torso) sensors and two arm sensors as discussed with the exemplary garment 401 illustrated in FIG. 4.

The garment 701 also comprises other sensors in addition to ECG sensors. For example, the garment 701 comprises a body temperature sensor 761 that operates to measure the body temperature of a wearer of the garment 701. Though the body temperature sensor 761 is illustrated on the chest of the garment 701 for illustrative clarity, such sensor 761 may be positioned anywhere on the garment 701 or off the garment 701, depending on the type of body temperature monitoring desired. The body temperature sensor 761 may be communicatively coupled to the central location 750 of the garment 701 (e.g., for communication and/or electrical power).

The garment 701 additionally comprises an air sensor 762 that operates to measure temperature and humidity of the air in which the wearer of the garment 701 is located. Though the air sensor 762 is illustrated near the waist of the garment 701 for illustrative clarity, such air sensor 762 may be positioned anywhere on the garment 701 (e.g., on the shoulder, on the back, on a relatively loose portion of the garment 701 away from the wearer's body, etc.) or off the garment 701, depending on the type of air monitoring desired. In an exemplary configuration, an extra layer of thermally insulative fabric and/or a moisture isolation layer may be disposed on the garment 701 between the air sensor 762 and the body of the garment wearer to reduce the impact of body temperature and/or moisture on the air sensor measurements. The air sensor 762 may be communicatively coupled to the central location 750 of the garment 701 (e.g., for communication and/or electrical power).

Figure 8:
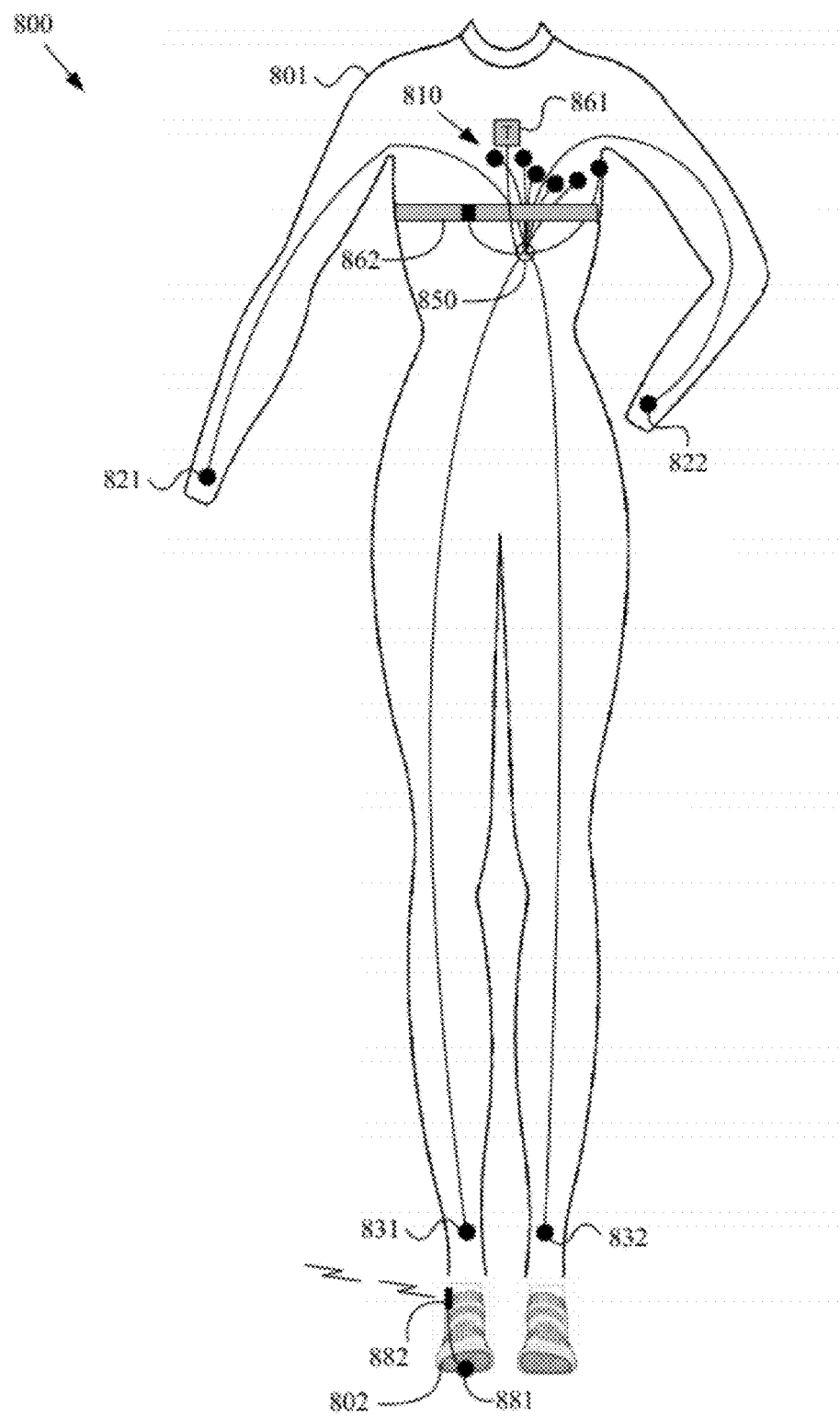
FIG. 8 is a diagram illustrating an exemplary garment (e.g., body suit and socks) health-monitoring system, in accordance with various aspects of the present invention.

FIG. 8 is a diagram illustrating an exemplary garment (e.g., body suit and socks) health-monitoring system 800, in accordance with various aspects of the present invention. The system 800 may, for example, share any or all characteristics of the exemplary systems 100-700 illustrated at FIGS. 1-7 and discussed previously.

The exemplary system 800 comprises a first garment 801 (e.g., a body suit) and a second garment 802 (e.g., a sock). The first garment 801 and the second garment 802 each comprise health sensors integrated into the garments 801 and 802. For example, the first garment 801 comprises ECG sensors 810, 821, 822, 831 and 832, which may share any or all characteristics with similar sensors 110, 121, 122, 131 and 132 of the garment 101 illustrated in FIG. 1 and discussed previously. Also for example, the first garment 801 comprises a body temperature sensor 861 and breath rate (or respiratory rate) sensor 862, which may share any or all characteristics with similar sensors 661 and 662 of the garment 601 illustrated in FIG. 6 and discussed previously. The exemplary sensors of the first garment 801 may, for example, be conductively and/or communicatively coupled to the central location 850 for access to such sensors by monitoring, analyzing and/or communicating circuitry, and/or for access to electrical power if needed.

As discussed previously, health analysis may comprise analyzing signals associated with any of a variety of different types of sensors in combination. As another illustration of such combination, the second garment 802 comprises an impact sensor 881 that operates to determine stepping rate and/or force. Such a sensor 881 may, for example, provide insight into the type of activity in which the wearer of the second garment 802 is engaging. The sensor 881 is coupled to a wireless transmitter 882, which operates to communicate information from the impact sensor 881 to another system component for analysis. As will be discussed in more detail later, such a wireless transmitter 882 may operate in accordance with any of a variety of standard and/or propriety communication protocols. In an exemplary scenario, a processing component may operate to access cardiac sensor information, body temperature information and breath rate information at the central location 850 and operate to access impact sensor information from the wireless transmitter 882 wirelessly. Such an exemplary scenario illustrates that information corresponding to different respective sensors may flow through different respective types of information paths to the ultimate processor of such information.

Figure 9:
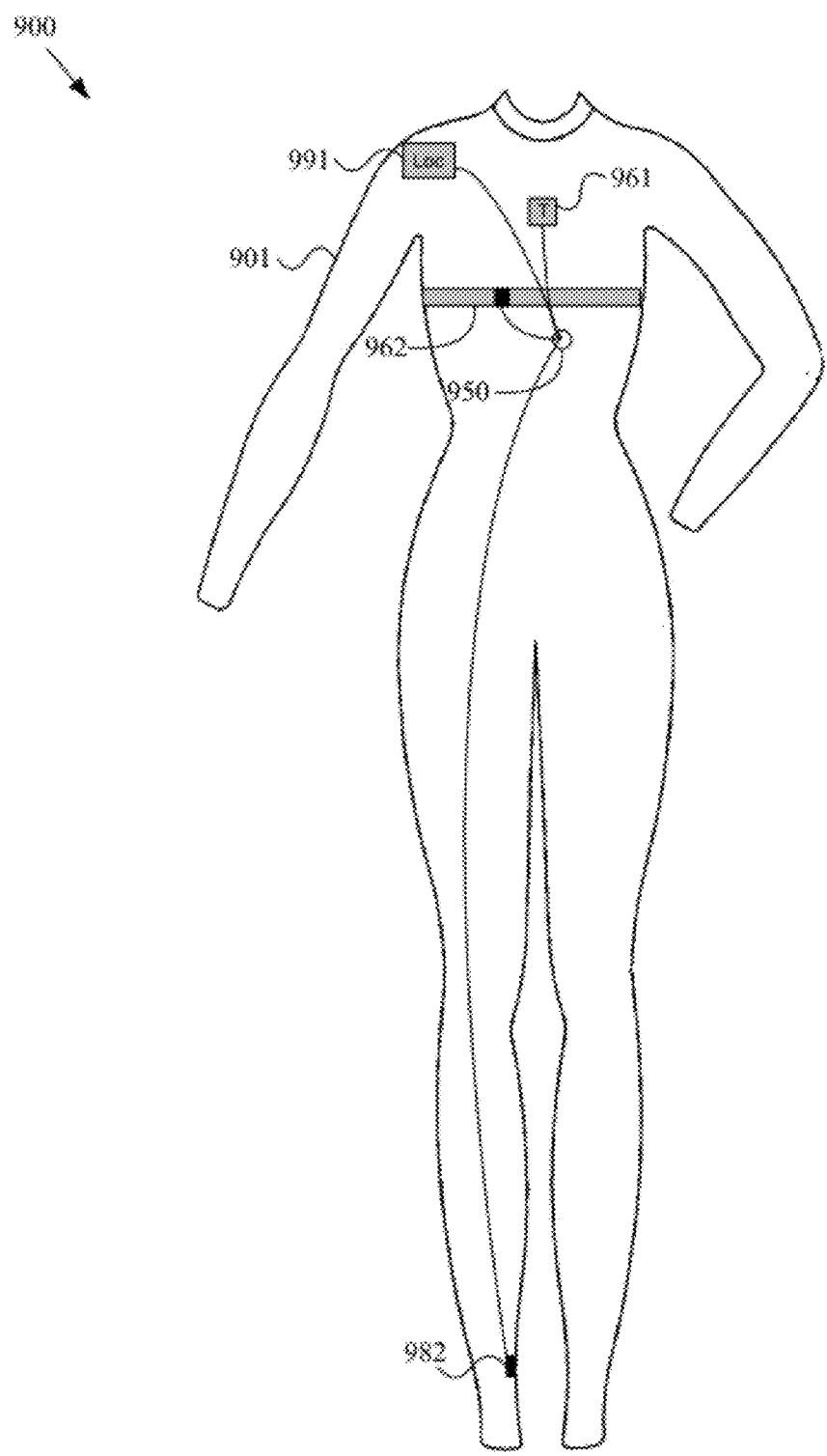
FIG. 9 is a diagram illustrating an exemplary garment (e.g., body suit) health-monitoring system, in accordance with various aspects of the present invention.

FIG. 9 is a diagram illustrating an exemplary garment (e.g., body suit) health-monitoring system 900, in accordance with various aspects of the present invention. The system 900 may, for example, share any or all characteristics of the exemplary systems 100-800 illustrated at FIGS. 1-8 and discussed previously.

The exemplary system 900 comprises a garment 901 (e.g., a body suit). The garment 901 and comprises health sensors integrated into the garment 901. For example, the garment 901 comprises a body temperature sensor 961 and breath rate (or respiratory rate) sensor 962, which may share any or all characteristics with similar sensors 661 and 662 of the garment 601 illustrated in FIG. 6 and discussed previously. Also for example, the garment 901 comprises an impact sensor 982 integrated with the garment 901 near the right ankle Additionally, for example, the garment 901 comprises a location sensor 991 (e.g., GPS based, cellular triangulation based, etc.) integrated with the garment 901 near the right shoulder. The exemplary sensors of the garment 901 may, for example, be conductively and/or communicatively coupled to the central location 950 for convenient access to such sensors by monitoring, analyzing and/or communicating circuitry, and/or for access to electrical power if needed.

As discussed previously, health analysis may comprise analyzing signals associated with any of a variety of different types of sensors in combination. As another illustration of such combination, the garment 901 comprises two physiological sensors (i.e., the body temperature sensor 961 and breath rate sensor 962), an environmental sensor (i.e., the location sensor 991) and a situational (or activity) sensor (i.e., the impact sensor 982).

In an exemplary scenario, monitoring, analyzing and/or communicating circuitry may operate to access body temperature sensor signals (or information), breathing rate sensor signals (or information), location sensor signals (or information) and impact signals (or information) at the central location 950. As illustrated in FIG. 8, however, access to such signals (or information) may occur via different respective types of communication links with different respective sensor circuitry.

Figure 10:
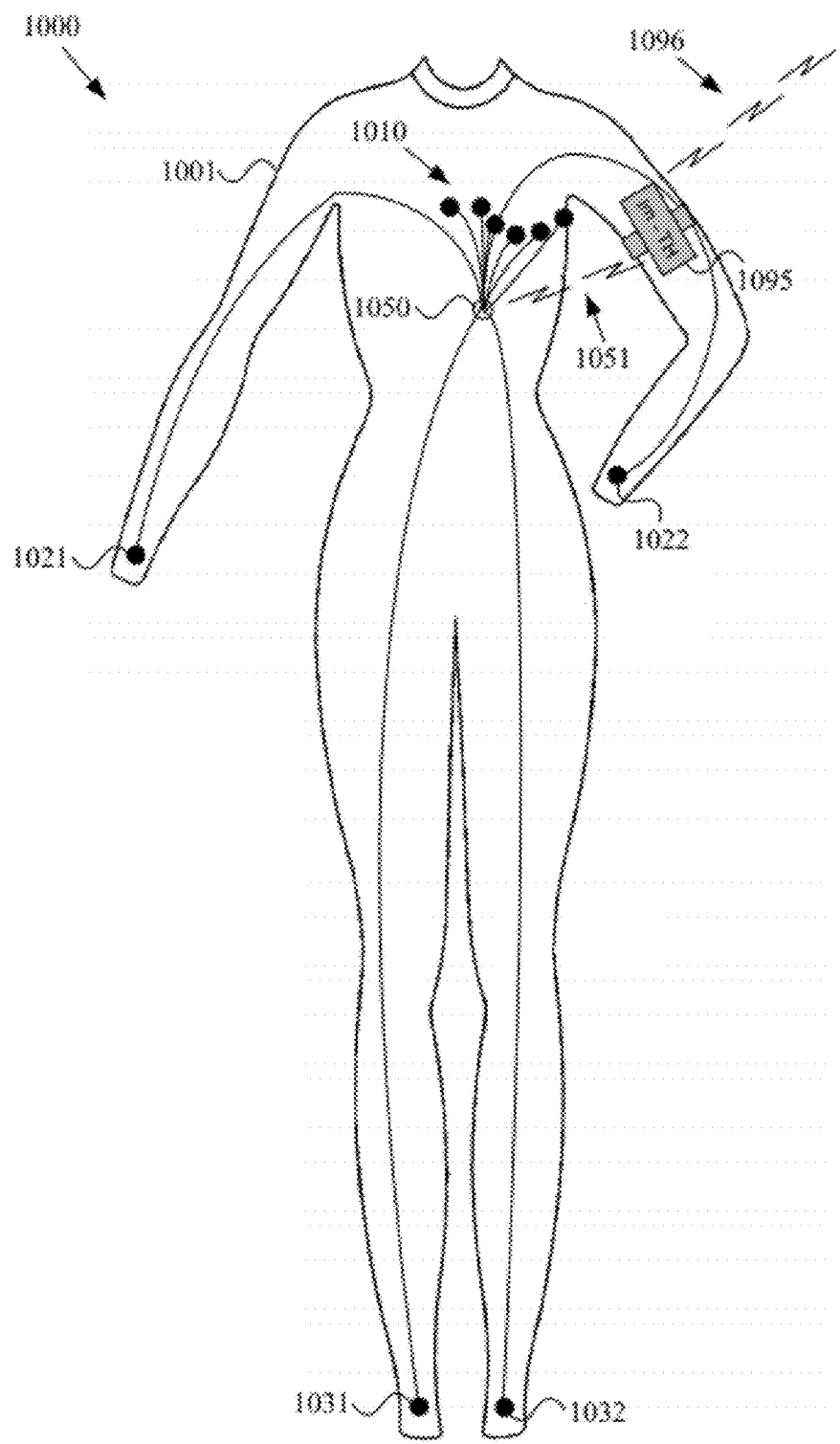
FIG. 10 is a diagram illustrating an exemplary garment (e.g., body suit) health-monitoring system, in accordance with various aspects of the present invention.

FIG. 10 is a diagram illustrating an exemplary garment (e.g., body suit) health-monitoring system 1000, in accordance with various aspects of the present invention. The system 1000 may, for example, share any or all characteristics of the exemplary systems 100-900 illustrated at FIGS. 1-9 and discussed previously.

The exemplary system 1000 comprises a garment 1001 (e.g., a body suit) and a non-garment arm-band 1095. The garment 1001 and the non-garment armband 1095 each comprise health sensors. For example, the garment 1001 comprises ECG sensors 1010, 1021, 1022, 1031 and 1032, which may share any or all characteristics with similar sensors 110, 121, 122, 131 and 132 of the garment 101 illustrated in FIG. 1 and discussed previously. The exemplary sensors of the garment 1001 may, for example, be conductively and/or communicatively coupled to the central location 1050 for access to such sensors by monitoring, analyzing and/or communicating circuitry.

As discussed previously, health analysis may comprise analyzing signals associated with any of a variety of different types of sensors in combination, where some of such sensors may be incorporated into a garment and others of such sensors may be off-garment. As another illustration of such combination, the non-garment armband 1095 comprises an impact sensor Im that operates to determine stepping rate and/or force. Such a sensor Im may, for example, provide insight into the type of activity in which the wearer of the armband 1095 is engaging. Additionally, the armband 1095 comprises an air temperature and humidity sensor TH that operates to determine air temperature and humidity. Such a sensor TH may, for example, provide insight into the environmental conditions in which a wearer of the armband 1095 is performing. The armband sensors are coupled to a wireless transmitter in the armband 1095, which in turn is communicatively coupled to the central location 1050 of the garment 1001 via a wireless RF communication link 1051. Monitoring, analyzing and/or communicating circuitry (discussed later) may, in turn, operate to access the impact and air information from the armband 1095 sensors at the central location 1050 of the garment 1001.

Figure 11:
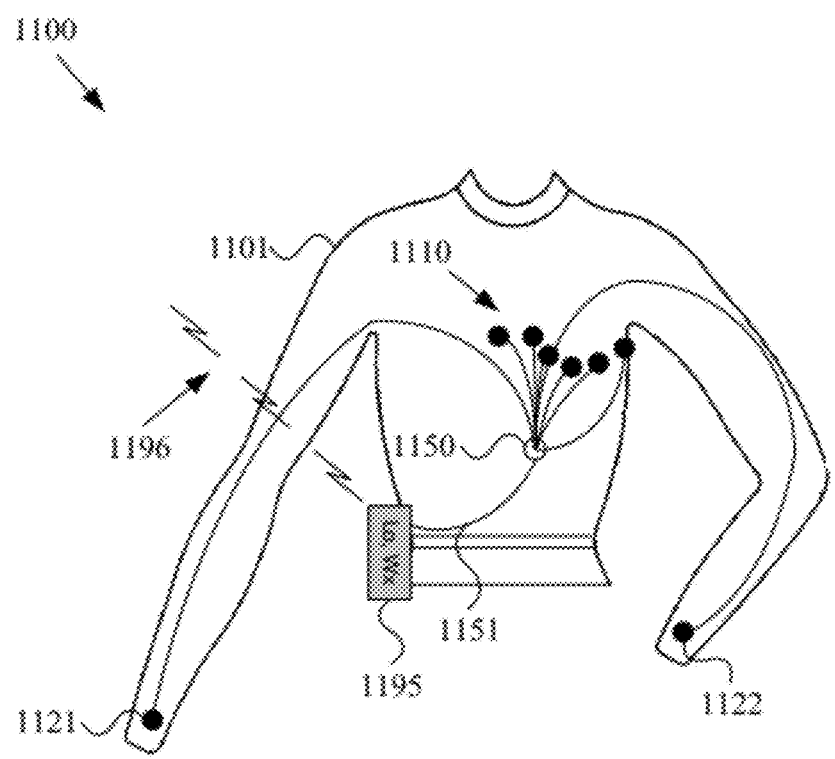
FIG. 11 is a diagram illustrating an exemplary garment (e.g., shirt) health-monitoring system, in accordance with various aspects of the present invention.

FIG. 11 is a diagram illustrating an exemplary garment (e.g., shirt) health-monitoring system 1100, in accordance with various aspects of the present invention. The system 1100 may, for example, share any or all characteristics of the exemplary systems 100-1000 illustrated at FIGS. 1-10 and discussed previously.

The exemplary system 1100 comprises a garment 1101 (e.g., a shirt) and a non-garment device 1195 that may be worn with (e.g., attached to or worn separately from) the garment 1101. The garment 1101 and the non-garment device 1195 each comprise health sensors. For example, the garment 1101 comprises ECG sensors 1110, 1121 and 1122, which may share any or all characteristics with similar sensors 310, 321 and 322 of the garment 301 illustrated in FIG. 3 and discussed previously. The exemplary sensors of the garment 1101 may, for example, be conductively and/or communicatively coupled to the central location 1150 for convenient access to such sensors (e.g. access to signals and/or information associated with such sensors) by monitoring, analyzing and/or communicating circuitry.

As discussed previously, health analysis may comprise analyzing signals associated with any of a variety of different types of sensors in combination, where some of such sensors may be incorporated into a garment and others of such sensors may be off-garment. As another illustration of such combination, the non-garment device 1195 comprises a weather sensor Wx that operates to determine characteristics of weather in which a wearer of the device 1195 may be operating. Such a sensor Wx may, for example, be a self-contained weather-sensing device or may comprise communication circuitry with which to communicate with weather stations (e.g., via a wireless communication link 1196). Additionally, the device 1195 comprises a location sensor Lo (e.g., GPS based, cellular triangulation based, etc.) that operates to determine the location of the device 1095. Such location may, for example, be expressed in any number of dimensions, including for example, longitude, latitude, elevation, etc.

The device 1195 is communicatively coupled to the central location 1150 of the garment 1100 by one or more conductors 1151 (e.g., integrated into the garment 1150 and/or separate from the garment). In various exemplary scenarios, some of which will be discussed below, monitoring, analyzing and/or communication circuitry may operate to access sensor information in any of a variety of manners. In the exemplary system 1100 of FIG. 11, the device 1195 operates to access cardiac sensor information at the central location 1150 of the garment 1101 via the one or more conductors 1151. The device 1195 may also access location and/or weather information internally, and/or for access to electrical power if needed.

Also, as will be discussed in more detail below, various aspects of the present invention include the communication of health information (e.g., sensor readings, sensor analysis results, warning information, instructions for the subject to follow, etc.) with entities distant from the subject. Such communication may, for example, occur between the system 1100 (or device 1195) and health care professionals, emergency services, health care databases, a user's home computer, etc. Such communication may, for example, be performed by the device 1195 via one or more wireless communication links 1196.

As explained above, the previous discussions of FIGS. 1-11 provided various non-limiting examples of garment/sensor configurations and/or operation. It should be noted that such examples are for illustrative purposes only and are not meant to be limiting. Accordingly, the scope of various aspects of the present invention should not be limited by characteristics of any of such specific examples unless explicitly claimed.

The discussion of various aspects of the present invention will now shift to various manners of monitoring, analyzing and/or communicating information related to various garment sensor systems. In particular, the following discussions of FIGS. 12-14 will now provide various non-limiting examples of such monitoring, analyzing and/or communicating. It should be noted that such examples are for illustrative purposes only and are not meant to be limiting. Accordingly, the scope of various aspects of the present invention should not be limited by characteristics of any of such examples unless explicitly claimed.

Figure 12:
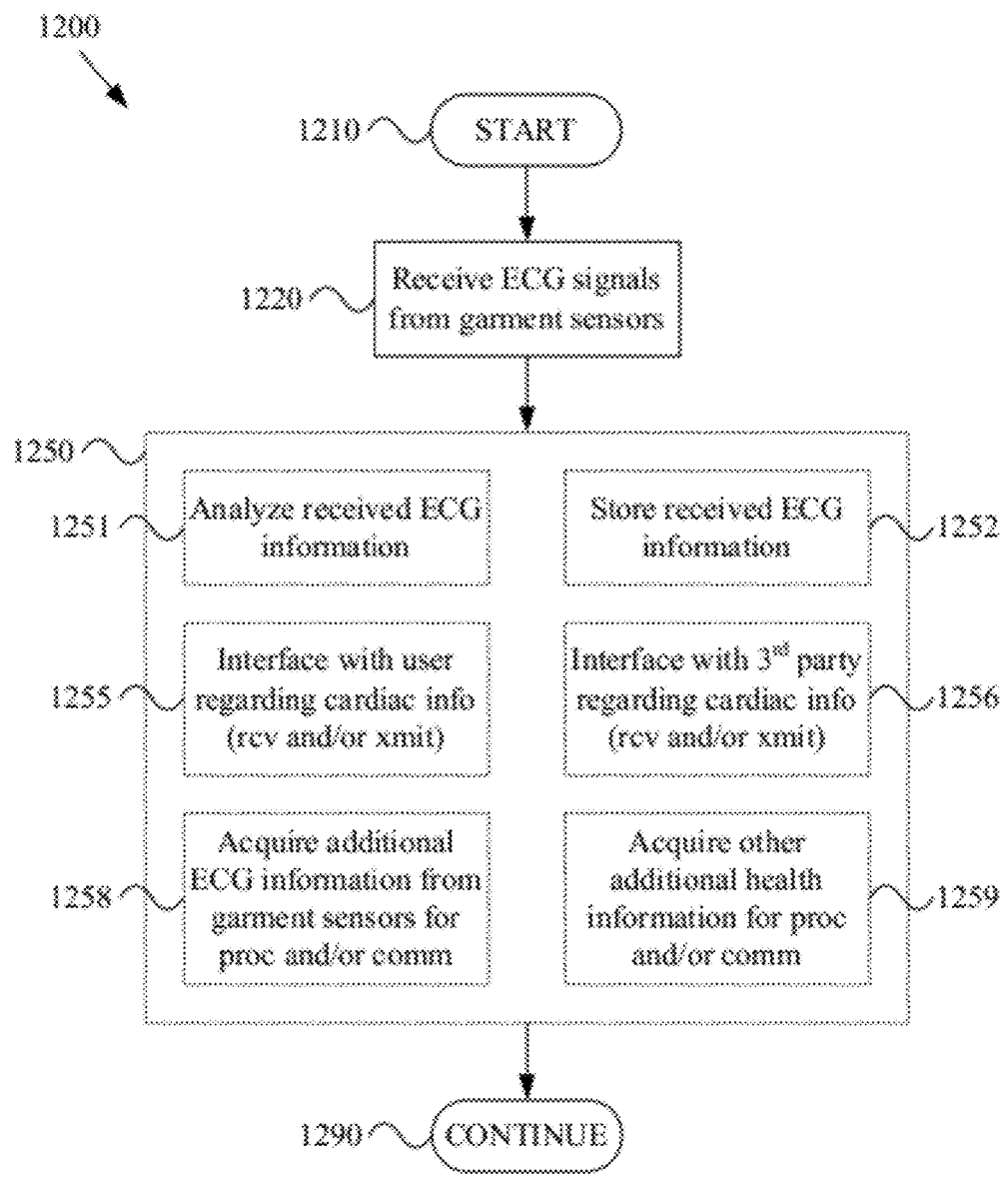
FIG. 12 is a flow diagram illustrating an exemplary method (e.g., in a garment system) for acquiring and/or processing electrocardiogram information of a user, in accordance with various aspects of the present invention.

FIG. 12 is a flow diagram illustrating an exemplary method 1200 (e.g., in a garment system) for acquiring and/or processing electrocardiogram information of a user, in accordance with various aspects of the present invention.

The exemplary method 1200 may begin executing at step 1210. The Exemplary method 1200 may begin executing for any of a variety of causes and/or conditions, non-limiting examples of which will now be provided. For example, the method 1200 may begin executing in response to a local user command to begin. For example, a wearer of a garment comprising health sensors may enter a user command to begin execution. Also for example, the method 1200 may begin executing in response to receiving a command from a remote location. For example, a health care provider, a family member, emergency personnel, and the like may remotely command a system implementing the method 1200 to begin execution.

Additionally for example, the exemplary method 1200 may begin executing in response to detecting that a subject is wearing a portion and/or all of a health-monitoring system implementing the method 1200. For example, the method 1200 may begin executing in response to detecting that a subject is wearing a garment comprising integrated sensors, wearing and/or using an electronic device that implements a portion or all of the exemplary method 1200, etc. Also for example, the exemplary method 1200 may begin executing in response to user initiation of a computer application, the execution of which causes a processor to implement a portion or all of the exemplary method 1200.

Additionally for example, the exemplary method 1200 may begin executing in response to a timer. For example, the method 1200 may begin execution when the time-of-day enters a particular window. For example, the method 1200 may begin executing at the beginning of a time window associated with high stress and/or physical activity (e.g., during rush hour, during a regular morning workout, etc. Also for example, the method 1200 may begin execution on a periodic basis (e.g., every 10 minutes, etc.).

Further for example, the exemplary method 1200 may begin executing in response to detected physiological signals. For example, the exemplary method 1200 may begin executing in response to detecting an elevated body temperature and/or heart rate. Also for example, the exemplary method 1200 may begin executing in response to detecting a respiration rate that is higher than a particular threshold and/or lower than a particular threshold. Additionally for example, the exemplary method 1200 may begin executing in response to detecting a signal from a neurological-sensor indicating that the subject is experiencing pain and/or a exceeding a particular level of pain.

Also for example, the exemplary method 1200 may begin executing in response to detected environmental characteristics. For example, the method 1200 may begin executing in response to detecting a user moving from a relatively cool air-conditioned environment to a relatively hot humid outdoor environment. Also for example, the method 1200 may begin executing in response to detecting that the user has moved into full sunlight and/or has been in positioned in full sunlight for a particular amount of time. Additionally for example, the method 1200 may begin executing in response to detecting outside air temperature above and/or below respective thresholds. For example, the method 1200 may begin executing in response to detecting that an elevation above a particular level. Also for example, the method 1200 may begin executing in response to a detected location (e.g., in response to detecting a location associated with an exercise facility, a location associated with a high-stress and/or high-excitement environment, etc.).

Also for example, the exemplary method 1200 may begin executing in response to detected situational (or activity) characteristics. For example, the method 1200 may begin executing in response to detecting that a subject is running, in response to detecting that a subject is lifting a relatively heavy weight, in response to detecting that a subject has not moved for a particular amount of time, in response to determining that a subject is unconscious and/or dreaming, etc.

Still further for example, the exemplary method 1200 may begin executing in response to any combination of the above mentioned causes and/or conditions. In general, the method 1200 may begin executing in response to any of a variety of causes and/or conditions. Accordingly, the scope of various aspects of the present invention should not be limited by characteristics of any particular causes and/or conditions, or combinations thereof, unless specifically claimed.

The exemplary method 1200 may, at step 1220, comprise receiving electrocardiogram (ECG) signals from garment sensors. Step 1220 may comprise receiving such signals in any of a variety of manners, non-limiting examples of which will now be provided.

The previous discussion of FIGS. 1-11 provided many examples of ECG sensors incorporated into garments. Step 1220 may comprise receiving ECG signals associated with any or all of such sensors. In general, when the following discussion discusses receiving and/or processing a sensor signal, such reference generally refers to any signal associated with a sensor. Such a signal may, for example, comprise a raw unprocessed signal from an electrode, such a signal may comprise a data signal communicating digital data associated with a sensor reading or other sensor information, etc.

For example, step 1220 may comprise receiving ECG signals at a common location of a garment. As illustrated in FIGS. 1-11, conductive paths (e.g., conductive fibers, conductive strips, etc.) may be formed into a garment to provide access to all ECG electrodes at a single convenient location. In such a scenario, step 1220 may comprise receiving (e.g., with ECG circuitry located at or near the central location) respective ECG signals associated with each of a plurality of ECG electrodes integrated into a garment. Additionally for example, step 1220 may comprise receiving a wireless signal communicating ECG sensor reading information (e.g., a wireless signal describing one or more voltage potential differences, etc.). In such a wireless scenario, step 1220 may comprise receiving a wireless signal communicated in accordance with any of a variety of standard and/or proprietary communication protocols (e.g., body area network protocols, personal area network protocols, local area network protocols, metropolitan area network protocols, cellular communication network protocols, satellite communication network protocols, Internet protocols, etc.). Such a protocol may, for example, comprise specific features (e.g. messages, message sequences, packet structures, packet fields, etc.) that are specifically adapted to the communication of ECG information and/or other health-related information.

For example, step 1220 may comprise receiving the ECG signals separately, combined into a single data structure or packet, combined with signals associated with other physiological and/or non-physiological sensors, etc. For example, step 1220 may comprise receiving the ECG signals at a device integrated with the garment. Also for example, as exemplified at FIGS. 10 and 11, step 1220 may comprise receiving the ECG signals at a device separate from the garment but worn by (or positioned near) the user. Additionally, as exemplified at FIG. 11 (e.g., via a communication link 1196), step 1220 may comprise receiving the ECG signals at a location remote from the user (e.g., at user equipment at a remote premises, at a health care facility, at an emergency vehicle, at a doctor's cellular telephone, etc.).

In general, step 1220 may comprise receiving electrocardiogram (ECG) signals from garment sensors. Accordingly, the scope of various aspects of the present invention should not be limited by characteristics of any particular manner of receiving such signals or by characteristics of any particular type of signal unless explicitly claimed.

The exemplary method 1200 may, at step 1250, comprise analyzing the ECG signals (e.g., ECG signals received at step 1220) to ascertain the cardiovascular health of the garment wearer. Step 1250 may comprise analyzing the ECG signals in any of a variety of manners, non-limiting examples of which will now be provided. Additional examples of such analysis may be found in U.S. patent application Ser. No. 11/492,278, filed Jul. 25, 2006, and titled "Mobile Communication Device and Other Devices with Cardiovascular Monitoring Capability", the contents of which are hereby incorporated herein in their entirety by reference.

Step 1250 will now be exemplified by various different types of analysis that may be performed. The following discussion of step 1250 is divided into non-limiting exemplary sub-steps for the sake of illustrative clarity. Step 1250 may, for example, comprise any or all characteristics of such exemplary sub-steps.

Step 1250 may, for example at sub-step 1251, comprise analyzing received ECG information. Such analysis may, for example, comprise analyzing the ECG information in light of various cardiac pathologies. Such pathologies may, for example and without limitation, comprise various ischemic diseases, acute coronary syndrome (ischemic chest pain), acute myocardial infarction (heart attacks), arrhythmias tachyarrhythmias (fast rate disturbances), bradyarrhythmias (slow rate disturbances), etc. Although the following discussion generally provides illustrations of processing cardiac information in light of such pathologies, the scope of various aspects of the present invention should not be limited by characteristics of particular pathologies or pathologies in general. For example, various aspects of the present invention may apply equally to non-pathology cardiac areas. For example and without limitation, various aspects of the present invention may also apply to cardiac information related to general health monitoring, fetus monitoring, medication effectiveness monitoring, etc.

Cardiac (or ECG) signals may, for example, comprise a primary component (e.g., frequency component) and a variety of residual components (or harmonic components). Substep 1251 may, for example, comprise analyzing cardiac information by, at least in part, analyzing a primary component of a cardiac signal. For example, sub-step 1251 may comprise analyzing the cardiac information by, at least in part, comparing a primary component characteristic of the cardiac signal to one or more primary component characteristics associated with a known cardiac pathology. Such a primary component characteristic may, without limitation, comprise frequency, signal level, signal shape or statistical characteristics (e.g., medium value, mean value, variance, standard deviation, etc.).

Sub-step 1251 may, for example, comprise processing current cardiac information and previous cardiac information (e.g., generally corresponding to a first cardiac signal and at least a second cardiac signal). For example and without limitation, sub-step 1251 may comprise analyzing cardiac information by determining a difference between a current cardiac signal (e.g., a primary component thereof) and at least one previous cardiac signal or baseline signal (e.g., a primary component thereof) and determining the existence of a cardiac pathology based, at least in part, on the determined difference. For example, sub-step 1251 may comprise determining the existence of a cardiac pathology by comparing the determined difference to at least one difference characteristic associated with a known cardiac pathology.

In a non-limiting exemplary scenario, sub-step 1251 may comprise comparing changes in a cardiac signal to known pathologic patterns (e.g., ST-segment depression or ST-segment elevation). As mentioned previously, analysis of cardiac signal (or information) changes over time may comprise analyzing changes in heart rate or other heart characteristics (e.g., to monitor effectiveness of anti-arrhythmic medication, blood pressure medication or other medication).

Sub-step 1251 may, for example, comprise processing current and previous cardiac information corresponding to any of a variety of time intervals. For example and without limitation, sub-step 1251 may comprise determining short-term or long-term differences in a cardiac signal and to analyze such short-term or long-term differences.

Sub-step 1251 may, for example, comprise processing more than two cardiac signals. For example and without limitation, the sub-step 1251 may comprise analyzing cardiac information by determining a trend between a current cardiac signal (e.g., a primary component thereof) and at least two previous cardiac signals (e.g., respective primary components thereof) and determining the existence of a cardiac pathology based, at least in part, on the determined trend. For example, sub-step 1251 may comprise determining the existence of a cardiac pathology by comparing the determined trend to at least one trend characteristic associated with a known cardiac pathology.

Sub-step 1251 may also, for example, comprise analyzing cardiac information by, at least part, analyzing one or more residual (or harmonic) components of a cardiac signal. For example, sub-step 1251 may comprise comparing one or more residual component characteristics of the cardiac signal to one or more residual component characteristics associated with a known cardiac pathology. Such residual characteristics may, without limitation, comprise frequency, signal level, signal shape or statistical characteristics (e.g., median value, mean value, variance, standard deviation, etc.).

As mentioned previously, sub-step 1251 may, for example, comprise processing current cardiac information and previous cardiac information (e.g., generally corresponding to a first cardiac signal and at least a second cardiac signal). For example and without limitation, sub-step 1251 may comprise analyzing cardiac information by determining a difference between a current cardiac signal (e.g., at least one residual component thereof) and at least one previous cardiac signal (e.g., at least one residual component thereof) and determining the existence of a cardiac pathology based, at least in part, on the determined difference. For example, sub-step 1251 may comprise determining the existence of a cardiac pathology by comparing the determined difference to at least one difference characteristic associated with a known cardiac pathology.

Also as mentioned previously, sub-step 1251 may, for example, comprise processing more than two cardiac signals. For example and without limitation, sub-step 1251 may comprise analyzing cardiac information by determining a trend between a current cardiac signal (e.g., at least one residual component thereof) and at least two previous cardiac signals (e.g., respective residual components thereof) and determining the existence of a cardiac pathology based, at least in part, on the determined trend. For example, sub-step 1251 may comprise determining the existence of a cardiac pathology by comparing the determined trend to at least one trend characteristic associated with a known cardiac pathology.

Sub-step 1251 may, for example, comprise performing spectral analysis of various cardiac signals (or signals derived therefrom). For example and without limitation, the sub-step 1251 may comprise performing spectral analysis on a cardiac signal by, at least in part, comparing the frequency spectrum of the cardiac signal (e.g., a primary component or residual components thereof) with a frequency spectrum associated with a known cardiac pathology. Further for example, sub-step 1251 may comprise determining a difference (or trend) between a current cardiac signal and at least one previous cardiac signal, and determining the existence of a cardiac pathology based, at least in part, on spectral analysis of the determined difference (or trend).

As mentioned previously, various types of cardiac (or ECG) information may be obtained using audio monitoring or acoustical sensing (or detecting) devices (e.g., in lieu of or in addition to electrical electrodes). Sub-step 1251 may, for example and without limitation, comprise processing such information to determine various cardiovascular characteristics. For example and without limitation, such characteristics may comprise characteristics relating to blood pressure, contractility, blood flow and turbulence, etc. As discussed previously, cardiac information may be acquired from any of a variety of sources. Such information (e.g., digital and/or analog signals) may be analyzed (e.g., at sub-step 1251) to determine any of a large variety of cardiac conditions. Accordingly, the scope of various analysis aspects of the present invention should not be limited by characteristics of cardiac (or ECG) information obtained from any particular source (e.g., an electrode source, audio monitoring source, etc.).

Sub-step 1251 may, for example, comprise determining an action to take based on results of cardiac (or ECG) signal analysis. For example, sub-step 1251 may comprise, based at least in part on cardiac signal analysis, determining to generate (or initiate generation of) an alert message. For example and without limitation, the alert message may comprise characteristics of an alert message directed to the subject wearing the garment comprising the cardiac sensors. For example, sub-step 1251 may comprise utilizing any of a variety of user interface mechanisms (e.g., integrated in the garment, on a proximate portable electronic device of the user, etc.) to generate such an alert message.

Also for example, sub-step 1251 may comprise communicating (or causing the communication of) an alert message to another system. For example, sub-step 1251 may comprise communicating with a physician's system, a system of a health-care facility, a system of an emergency response team, a 911 emergency service, etc. Step 1251 may, for example, utilize one or more communication interface modules of the system implementing the exemplary method 1200 to perform such communication.

Additionally for example, sub-step 1251 may comprise, based at least in part on cardiac signal analysis, conducting a two-way communication and/or control session with a remote system. In a non-limiting exemplary scenario, sub-step 1251 may comprise providing user health (e.g., ECG-related) information to a health-care facility system and/or health-care facility personnel, who may in turn communicate information back to the user system implementing the method 1200. For example, a health-care facility may communicate requests to the system implementing the method 1200 for additional information (e.g., additional cardiac information, user information, baseline ECG information, additional information from other physiological and/or non-physiological sensors, location information, etc.). In response to such requests, the system implementing the method 1200 may acquire, analyze and/or communicate additional requested information to the requestor.

Also for example, sub-step 1251 may comprise establishing a line of communication by which a health-care facility may communicate instruction information to the user and/or a person near the user (e.g., behavior instructions, first aid instructions, etc.). Additionally for example, a physician and/or emergency technician may conduct a two-way voice communication with a user of the system implementing the method 1200.

Sub-step 1251 may, for example, be performed by one or more processors. Such processor(s) may, for example, be integrated in same garment as the ECG sensors and/or integrated in a different garment. Such processor(s) may also, for example, be located in a device (e.g., a personal electronic device) separate from the garment. Additionally, such processor(s) may be located at a premises (e.g., at a user's personal computing system, at a health-care provider's facility, in an emergency vehicle, etc.).

In general sub-step 1251 may comprise analyzing cardiac signals (e.g., ECG signals received at step 1220) to ascertain the cardiovascular health of the garment wearer. Accordingly, the scope of various aspects of the present invention should not be limited by characteristics of particular types of cardiac (or ECG) signals and/or characteristics of any particular manner of processing such signals unless explicitly claimed.

Step 1250 may, for example at sub-step 1252, comprise storing received cardiac (or ECG) information (e.g., as received at step 1220) and/or analysis results information corresponding to such received cardiac information (e.g., as determined at sub-step 1251). Sub-step 1252 may comprise performing such storage in any of a variety of manners, non-limiting examples of which will now be presented.

The stored information may, for example, include raw sensor data, the results of processed sensor data, information exchanged with the user regarding such sensor data, information exchanged with a remote site (e.g., a health care facility, emergency medical service, etc.), summaries of sensor data, baseline comparison data, etc.

For example, sub-step 1252 may comprise storing such information in a memory (e.g., a volatile and/or non-volatile memory device) that is integrated with the same garment in which the ECG sensors are integrated and/or integrated in a different garment. Sub-step 1252 may comprise storing such information in a user's personal off-garment database and/or storing such information in a central healthcare database (e.g., associated with one or more health care providers).

Such stored information may, for example, be retained for later analysis and/or for later communication to another device. For example, sub-step 1252 may comprise storing such information in a memory that may be read by another device that is within personal area network wireless range of the memory. Also for example, sub-step 1252 may comprise storing such information in a memory that may be read by another device via a hardwire port (e.g., a USB and/or FireWire port).

Sub-step 1252 may, for example, comprise storing information in response to a determination made at sub-step 1251 to store such information. In a non-limiting exemplary scenario, sub-step 1251 may comprise determining that a particular monitored heart characteristic (e.g., ECG characteristics) should be stored for later analysis and/or monitored over a period of time. In such exemplary scenario, sub-step 1252 may comprise performing the information storage identified at sub-step 1251. Sub-step 1251 may also, for example, comprise storing information in response to receiving a request from a remote system (e.g., a health-care facility, a physician, an emergency response service, etc.) to acquire and/or store such information.

In general, sub-step 1252 comprises storing received cardiac (or ECG) information (e.g., as received at step 1220) and/or analysis results information corresponding to such received cardiac information (e.g., as determined at sub-step 1251). Accordingly, the scope of various aspects of the present invention should not be limited by any particular memory location or type, and/or by any particular manner of performing such information storage unless explicitly claimed.

Step 1250 may, for example at sub-step 1255, comprise interfacing with a user regarding cardiac (or ECG) information and/or other related information. Sub-step 1255 may comprise performing such user interfacing in any of a variety of manners, non-limiting examples of which will now be presented. Various examples of such user interaction were also presented above.

Sub-step 1255 may, for example, comprise providing an alert to a user (e.g., the garment wearer) of the system implementing the method 1200. Such alert may, for example, be an audio alert, video alert and/or physical/tactile alert. For example, in an exemplary scenario in which sub-step 1251 analyzes ECG information and identifies a potential emergency situation, sub-step 1255 may comprise outputting an alert to the user.

In another exemplary scenario, for example in response to analysis performed at sub-step 1251, sub-step 1255 may comprise providing behavioral instructions to the user. For example, sub-step 1255 may comprise audibly and/or visibly outputting instructions to the user regarding steps to take to minimize risk (e.g., sit down, lie down, breathe deeply, slow down, walk, take a particular drug, dial 911, drink water, etc.). Also for example, sub-step 1255 may similarly provide first aid information to the user or another person near the user (e.g., CPR instructions, directions to cool down the user, inhaler directions, etc.).

In another exemplary scenario, sub-step 1255 may comprise conducting a two-way communication (e.g., audibly, textually, visually, etc.) with the user and/or a person near the user. For example, in response to a potentially dangerous cardiac condition detected at sub-step 1251, sub-step 1255 may comprise establishing a two-way communication link by which the user and emergency technicians may communicate. Such communication link establishment may, for example, comprise initiating a 911 call, initiating a direct phone call to a subject's cardiologist, etc.

Sub-step 1255 may, for example, comprise providing ECG results to a user. For example, sub-step 1255 may comprise outputting a graphical display of present ECG readings, a graphical display of ECG information that caused generation of an alert, etc. Sub-step 1255 may also, for example, comprise providing ECG analysis results to a user. For example, such results may be provided upon request by the user and/or automatically without interaction with the user. In such a scenario, sub-step 1255 may also comprise presenting historical ECG analysis results to a user so that a user may compare previous results to present results.

In yet another exemplary scenario, sub-step 1255 may comprise providing a user interface by which a user may request additional cardiac testing (e.g., ECG testing), by which a user may define testing, by which a user may input information requested by the system implementing the method 1200, etc. Also for example, since health information may be regarded as sensitive, sub-step 1255 may comprise interfacing with a user regarding the communication of user-health information (e.g., ECG information) to a particular destination for such information.

Additional examples of the communication of health-related information with a user may be found in U.S. patent application Ser. No. 11/492,278, filed Jul. 25, 2006, and titled "Mobile Communication Device and Other Devices with Cardiovascular Monitoring Capability", the contents of which are hereby incorporated herein in their entirety by reference.

In general, sub-step 1255 may comprise interfacing with a user regarding cardiac (or ECG) information and/or other related information. Accordingly, the scope of various aspects of the present invention should not be limited by characteristics of any particular manner of interfacing with a user and/or any particular type of user interface information unless explicitly claimed.

Step 1250 may, for example at sub-step 1256, comprise interfacing with a third party regarding cardiac (or ECG) information and/or other related information (e.g., as received at step 1220, as analyzed at sub-step 1251 and/or as stored at step 1252). Sub-step 1256 may comprise performing such third-party interfacing in any of a variety of manners, non-limiting examples of which will now be presented. Various examples of third party interaction were also presented above.

For example, sub-step 1256 may comprise interfacing with the third party in a manner that is transparent to the user (e.g., the garment wearer). In an exemplary scenario, sub-step 1256 may comprise interfacing with an ambulatory rehabilitation specialist while the subject is walking in the park, lifting weights at home, performing rehabilitation exercises at a gym, etc. Such communication may, for example, be two-way communication. For example, sub-step 1256 may comprise receiving behavioral instructions from the third party and providing such behavioral instructions to the user (e.g., at sub-step 1255), and transmitting cardiac sensor (ECG electrode) signal information from the user's garment to the third party while the user is implementing the behavioral instructions.

Additional examples of the communication of health-related information with a third party may be found in U.S. patent application Ser. No. 11/492,278, filed Jul. 25, 2006, and titled "Mobile Communication Device and Other Devices with Cardiovascular Monitoring Capability", the contents of which are hereby incorporated herein in their entirety by reference.

In another exemplary scenario, for example in a scenario in which sub-step 1251 determines that a serious emergency situation exists, sub-step 1256 may comprise initiating an emergency call on behalf of the user. During such an emergency communication, for example, sub-step 1256 may comprise communicating information describing the cardiac emergency, describing the sensor signal and/or analysis results that caused the initiation of the emergency communication, communicating user identity and/or location information, communicating user medical history information, communicating information identifying the user's physician(s), etc.

In such an emergency scenario, sub-step 1256 may also comprise receiving sensing and/or analysis requests from the third party regarding the user. For example, the third party may request that the system implementing the method 1200 identify sensing capabilities of the system and request that the system provide any desired sensor information within the capabilities of the system. For example, sub-step 1256 may comprise receiving a request from an emergency response team for respiratory rate information and body temperature information, a request for continual ECG results communication to the third party, etc.

In yet another exemplary scenario, sub-step 1256 may comprise routinely (e.g., in non-emergency situations) interacting with a health-care facility to upload cardiac (or ECG) monitoring and/or analysis results to the health-care facility. For example, in such a scenario, health care technicians and/or physicians can routinely monitor progress of a subject that is not necessarily in danger. For example, for a person undergoing rehab for joint surgery or a person suffering from influenza, sub-step 1256 may comprise periodically (e.g., every four hours) uploading ECG information to a health-care provider. Similarly, for an elderly person without any serious medical condition, who merely desires regular monitoring, sub-step 1256 may comprise occasionally (e.g., once per week, whenever a shirt comprising integrated ECG electrodes is worn, etc.) uploading ECG information to a third party (e.g., a health-care provider, a family member, a care giver, etc.).

In general, sub-step 1256 may comprise interfacing with a third party regarding cardiac (or ECG) information and/or other related information (e.g., as received at step 1220, as analyzed at sub-step 1251 and/or as stored at step 1252). Accordingly, the scope of various aspects of the present invention should not be limited by characteristics of any particular manner of interfacing with a third party and/or any particular type of third party interface information unless explicitly claimed.

Step 1250 may, for example at sub-step 1258, comprise acquiring additional ECG information from the garment sensors (or other sensors) for additional analysis and/or communication. Sub-step 1258 may comprise performing such acquisition in any of a variety of manners, non-limiting examples of which will now be presented.

As discussed above, a determination may be made to acquire additional sensor information (e.g., from sensors on the garment, from sensors on another garment, from off-garment sensors, etc.). Such a determination may, for example, be made in response to analysis performed at sub-step 1251, in response to a user request receive at sub-step 1255, in response to a third party request received at sub-step 1256, etc.

In response to such a determination, sub-step 1258 may comprise acquiring the additional sensor information. For example, sub-step 1258 may comprise continuing to monitor in-garment ECG sensors to acquire additional ECG information for the subject. Also for example, sub-step 1258 may comprise acquiring any of a variety of other types of sensor information, as identified and/or requested. In such an exemplary scenario, sub-step 1258 may then comprise communicating the additional acquired sensor (e.g., ECG) information to the requesting entity.

In general, sub-step 1258 may comprise acquiring additional ECG information from the garment sensors (or other sensors) for additional analysis and/or communication. Accordingly, the scope of various aspects of the present invention should not be limited by characteristics of any particular manner of performing such acquisition or of any particular type of additional acquired sensor information unless explicitly claimed.

Step 1250 may, for example at sub-step 1259, comprise acquiring additional user health information (e.g., from other sensors, from memory, etc.) for additional analysis and/or communication. Sub-step 1259 may comprise performing such acquisition in any of a variety of manners, non-limiting examples of which will now be presented.

As discussed above, a determination may be made to acquire additional sensor information (e.g., from sensors on the garment, from sensors on another garment, from off-garment sensors, etc.). Such a determination may, for example, be made in response to analysis performed at sub-step 1251, in response to a user request received at sub-step 1255, in response to a third party request received at sub-step 1256, etc. In response to such a determination, sub-step 1259 may comprise acquiring the additional information.

Such additional information may, for example, comprise information in addition to signals and/or information corresponding to on-garment ECG sensors. Such information may comprise any of a variety of characteristics, many of which were provided above. Such information may, for example, comprise information corresponding to other physiological and/or non-physiological sensors (e.g., different from the on-garment ECG sensors). Such information may, for example, comprise user identity and/or location information, medical history information, previously stored baseline ECG information, medical contact information, emergency family contact information, user allergy information, user insurance information, etc. Acquiring such information may, for example, comprise reading and/or analyzing sensor information, retrieving such information from a local and/or remote memory, acquiring such information directly from a user via user interface, etc.

Sub-step 1258 may then, for example, comprise providing such acquired information to an entity that requested such information (e.g., a module internal to the system implementing the method 1200, the user, a third party, etc.).

In general, sub-step 1258 may comprise acquiring additional user health information (e.g., from other sensors, from memory, etc.) for additional analysis and/or communication. Accordingly, the scope of various aspects of the present invention should not be limited by characteristics of any particular manner of performing such acquisition or of any particular type of additional acquired information unless explicitly claimed The exemplary method 1200 may, at step 1290, comprise performing continued operation. Such continued operation may comprise any of a variety of characteristics. For example, the characteristics of such continued operation may be determined based, at least in part, on the results of the analysis performed at step 1250. Various examples of such operation have already been presented. For example, step 1290 may comprise acquiring and/or analyzing additional physiological and/or non-physiological information, initiating and/or maintaining a communication with a third party, communication alert and/or instruction information with a user of a system implementing the method 1200 (e.g., the wearer of a garment in which the ECG sensors and/or the system implementing the method 1200 are integrated), etc.

The previous discussion of FIG. 12 focused primarily on monitoring, analyzing and/or communicating regarding cardiac information related to ECG sensors integrated in a garment worn by a user (or subject). It should be noted that the previous discussion of ECG sensors may be readily applied to a garment with any of a variety of different types of health-monitoring sensors integrated into the garment.

Figure 13:
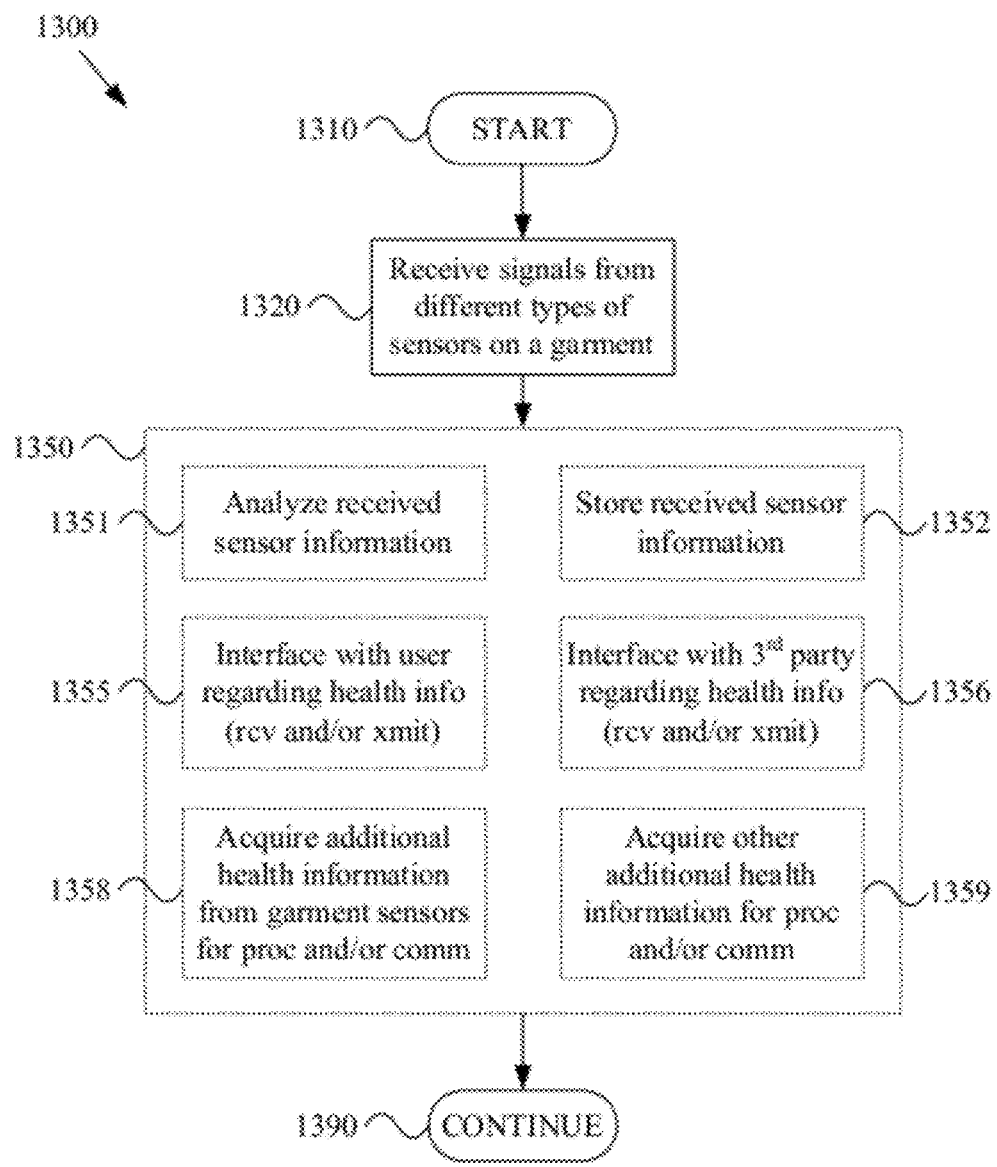
FIG. 13 is a flow diagram illustrating an exemplary method (e.g., in a garment system) for acquiring and/or processing health information of a user, in accordance with various aspects of the present invention.

Turning next to FIG. 13, such figure is a flow diagram illustrating an exemplary method 1300 (e.g., in a garment system) for acquiring and/or processing health information of a user, in accordance with various aspects of the present invention. While the previous discussion of FIG. 12 generally focused on cardiac (or ECG) sensors integrated into a garment (and the monitoring, analyzing and/or communicating associated therewith), the discussion of FIG. 13 will generally concern a garment in which a plurality of different types of sensors are integrated (and the monitoring, analyzing and/or communicating associated therewith).

The exemplary method 1300 may begin executing at step 1310. The exemplary method 1300 may begin executing for any of a variety of causes and/or conditions. Such causes and/or conditions may, for example, share any or all characteristics with the causes and/or conditions discussed previously with regard to step 1210 of the exemplary method 1200 illustrated in FIG. 12.

The exemplary method 1300 may, at step 1320, comprise receiving signals from a plurality of different types of sensors integrated into a garment. Step 1320 may comprise receiving such signals in any of a variety of manners, non-limiting examples of which will now be provided. For example, step 1320 may share any or all characteristics with step 1220 of the exemplary method 1200 illustrated in FIG. 12 and discussed previously.

The previous discussion of FIGS. 1-11 provided many examples of different types of sensors incorporated into garments. Step 1320 may comprise receiving signals associated with any or all of such sensors. In general, when the following discussion discusses receiving and/or processing a sensor signal, such reference generally refers to any signal associated with a sensor. Such a signal may, for example, comprise a raw unprocessed signal from an electrode or other sensor, such a signal may comprise a data signal communicating digital data associated with a sensor reading or other sensor information, etc.

For example, step 1320 may comprise receiving sensor signals at a common location of a garment. As illustrated in FIGS. 1-11, conductive paths (e.g., conductive fibers, conductive strips, etc.) may be formed into a garment to provide access to all sensors integrated into a garment at a single convenient location (e.g., a central location). In such a scenario, step 1320 may comprise receiving (e.g., with sensor-monitoring circuitry located at or near the central location) respective sensor signals associated with each of a plurality of different sensors and different types of sensors integrated into a garment.

Additionally for example, step 1320 may comprise receiving one or more wireless signals communicating sensor reading information (e.g., wireless signal(s) describing one or more physiological and/or non-physiological characteristics measured at one or more respective sensors integrated into the garment, etc.). In such a wireless scenario, step 1320 may comprise receiving such wireless signal(s) communicated in accordance with any of a variety of standard and/or proprietary communication protocols (e.g., body area network protocols, personal area network protocols, local area network protocols, metropolitan area network protocols, cellular communication network protocols, satellite communication network protocols, Internet protocols, etc.). Such a protocol may, for example, comprise specific features (e.g. messages, message sequences, packet structures, packet fields, etc.) that are specifically adapted to the communication of sensor-specific information and/or other health-related information.

For example, step 1320 may comprise receiving the sensor signals separately, combined into a single data structure or packet, combined with signals associated with other physiological and/or non-physiological sensors, etc. For example, step 1320 may comprise receiving the sensor signals at a device integrated with the garment. Also for example, as exemplified at FIGS. 10 and 11, step 1320 may comprise receiving the sensor signals at a device separate from the garment but worn by (or positioned near) the user. Additionally, as exemplified at FIG. 11 (e.g., via a communication link 1196), step 1320 may comprise receiving the sensor signals at a location remote from the user (e.g., at user equipment at a remote premises, at a health care facility, at an emergency vehicle, at a doctor's cellular telephone, etc.).

In general, step 1320 may comprise receiving signals from a plurality of different types of sensors integrated into a garment. Accordingly, the scope of various aspects of the present invention should not be limited by characteristics of any particular manner of receiving such signals or by characteristics of any particular type of signal unless explicitly claimed.

The exemplary method 1300 may, at step 1350, comprise analyzing the sensor signals (e.g., sensor signals received at step 1320) to ascertain the health (e.g., the cardiovascular health) of the garment wearer. Step 1350 may comprise analyzing the sensor signals in any of a variety of manners, non-limiting examples of which will now be provided. Step 1350 may, for example, share any or all characteristics with step 1250 of the exemplary method 1200 illustrated in FIG. 12 and discussed previously.

Step 1350 will now be exemplified by various different types of analysis that may be performed. The following discussion of step 1350 is divided into non-limiting exemplary sub-steps for the sake of illustrative clarity. Step 1350 may, for example, comprise any or all characteristics of such exemplary sub-steps.

Step 1350 may, for example at sub-step 1351, comprise analyzing received sensor information. Such analysis may, for example, comprise analyzing the received sensor information in light of various pathologies (e.g., in light of various cardiac pathologies). Sub-step 1351 may, for example, share any or all characteristics with the exemplary sub-step 1251 of the method 1200 illustrated in FIG. 12 and discussed previously.

Such previous discussion of sub-step 1251 generally focused on ECG sensor analysis. Such analysis techniques are also applicable to other types of physiological sensor analysis. Sub-step 1351 may be viewed as adding an additional dimension to the analysis discussed with regard to sub-step 1251. For example, since sub-step 1351 comprises analyzing received sensor information from a plurality of different types of sensors integrated into the garment, in an exemplary scenario involving cardiac (or ECG) sensor processing, sub-step 1351 may comprise analyzing such cardiac (or ECG) sensor signals in a particular context.

For example, when analyzing cardiac (e.g., ECG) information, a particular set of cardiac sensor characteristics may be of concern in a first physiological and/or non-physiological context but not of concern in a second such context. For example, an increase in heart rate while a person is at rest may be of more concern than an elevated hear rate while a person is in motion (e.g., while undergoing physical therapy, walking, running, swimming, etc.). Also for example, a sudden increase in body temperature may be of concern while a person is sleeping, but might not be of particular concern when a user is walking outdoors in hot sunny weather. The analysis of signals of different types of physiological sensor, the analysis of signals of both physiological sensors and environmental sensors, the analysis of signals of both physiological sensors and situational (or activity) sensors, and/or the analysis of signals of all of physiological sensors, environmental sensors and situational sensors, provides greater insight into the health state of the subject.

As another non-limiting example, the previous discussion of sub-step 1251 discussed comparing a current ECG with a previous (or baseline) ECG. In the scenario of sub-step 1351, such comparison may include selecting a baseline ECG for the comparison based on the determined context of the current ECG measurements. For example, a subject may have a plurality of baseline ECGs associated with the subject, each corresponding to a particular context. For example, a subject may have a baseline ECG associated with a sleep state, a baseline ECG associated with a moderate exercise state, a baseline ECG associated with an extreme exercise state, a baseline ECG associated with a rush-hour traffic situation, a baseline ECG associated with a rest state at a particular elevation, a baseline ECG associated with walking in hot and humid weather, etc. In such a scenario, sub-step 1351 may comprise analyzing signals from non-ECG sensors (e.g., impact sensors, temperature sensors, respiration rate sensors, location sensors, etc.) to identify a context and then select a context-dependent baseline ECG with which to compare a current ECG measurement.

For example, in an exemplary scenario, sub-step 1351 may comprise analyzing various non-ECG sensors and determine that the user is walking outside on a cool day. Sub-step 1351 may then, for example, comprise selecting a particular baseline ECG with which to compare a current ECG. In another exemplary scenario, sub-step 1351 may comprise analyzing various non-ECG sensors and determine that the user is shoveling snow. Sub-step 1351 may then, for example, comprise selecting a particular baseline ECG with which to compare a current ECG. Additionally, for example, in the snow-shoveling scenario, sub-step 1351 may comprise identifying snow-shoveling as an inherently dangerous cardiovascular activity, causing an increased level of analytical scrutiny and/or triggering communication with a health care facility for real-time monitoring by a health-care professional.

Also, as discussed previously with regard to sub-step 1251, various forms of cardiac analysis may comprise determining a trend in cardiac signals over time (e.g., long-term and/or short-term). Sub-step 1351 may, for example, comprise determining such a trend in cardiac signals in context. For example, sub-step 1351 may comprise determining a cardiac trend in the context of moderate exercise, in the context of sleeping, in the context of working, in the context of watching television, etc. Such consistency of context in trend analysis may increase the accuracy and/or reliability of cardiac analysis.

Similarly, context-dependent analysis may be incorporated into any or all of the cardiac analysis techniques discussed previously with regard to step 1251. Additionally, though the previous discussion is generally concerned with the analysis of cardiac (or ECG) signals in context, such context dependent analysis need not include cardiac analysis. For example, as illustrated at FIG. 9, a garment 901 may comprise integrated sensors that do not include cardiac sensors. In such an exemplary scenario, step 1351 may comprise analyzing respiratory rate (from respiratory rate sensor 962) and body temperature (from body temperature sensor 961) in light of a particular context ascertained by analyzing sensor information from the impact sensor 982 and location information from the location sensor 991. For example, step 1351 may comprise determining that increased breath rate and body temperature are normal in view of determining that the user is currently running. Conversely, step 1351 may comprise determining that an alert message should be issued to a health-care provider when an increased respiratory rate is detected with no apparent situational reason for such increase (e.g., the user is located in his living room in front of the television and not moving).

Sub-step 1351 may, for example, comprise determining an action to take based on results of sensor signal analysis. For example, sub-step 1351 may comprise, based at least in part on sensor signal analysis, determining to generate (or initiate generation of) an alert message. For example and without limitation, the alert message may comprise characteristics of an alert message directed to the subject wearing the garment comprising the cardiac sensors. For example, sub-step 1351 may comprise utilizing any of a variety of user interface mechanisms (e.g., integrated in the garment, on a proximate portable electronic device of the user, etc.) to generate such an alert message.

Also for example, sub-step 1351 may comprise communicating (or causing the communication of) an alert message to another system. For example, sub-step 1351 may comprise communicating with a physician's system, a system of a health-care facility, a system of an emergency response team, a 911 emergency service, etc. Step 1351 may, for example, utilize one or more communication interface modules of the system implementing the exemplary method 1300 to perform such communication.

Additionally for example, sub-step 1351 may comprise, based at least in part on sensor signal analysis, conducting a two-way communication and/or control session with a remote system. In a non-limiting exemplary scenario, sub-step 1351 may comprise providing user health (e.g., sensor-related) information to a health-care facility system and/or health-care facility personnel, who may in turn communicate information back to the user system implementing the method 1300. For example, a health-care facility may communicate requests to the system implementing the method 1300 for additional information (e.g., additional sensor information from other physiological and/or non-physiological sensors, user information, baseline sensor information, location information, etc.). In response to such requests, the system implementing the method 1300 may acquire, analyze and/or communicate additional requested information to the requestor.

Also for example, sub-step 1351 may comprise establishing a line of communication by which a health-care facility may communicate instruction information to the user and/or a person near the user (e.g., behavior instructions, first aid instructions, etc.). Additionally for example, a physician and/or emergency technician may conduct a two-way voice communication with a user of the system implementing the method 1300.

Sub-step 1351 may, for example, be performed by one or more processors. Such processor(s) may, for example, be integrated in same garment as the ECG sensors and/or integrated in a different garment. Such processor(s) may also, for example, be located in a device (e.g., a personal electronic device) separate from the garment. Additionally, such processor(s) may be located at a premises (e.g., at a user's personal computing system, at a health-care provider's facility, in an emergency vehicle, etc.).

In general sub-step 1351 may comprise analyzing sensor signals (e.g., sensor signals received at step 1320) to ascertain the health of the garment wearer. Accordingly, the scope of various aspects of the present invention should not be limited by characteristics of particular types of sensor signals and/or characteristics of any particular manner of processing such signals unless explicitly claimed.

Step 1350 may, for example at sub-step 1352, comprise storing received sensor information (e.g., as received at step 1320) and/or analysis results information corresponding to such received cardiac information (e.g., as determined at sub-step 1351). Sub-step 1352 may comprise performing such storage in any of a variety of manners, non-limiting examples of which will now be presented.

The stored information may, for example, include raw sensor data, the results of processed sensor data, information exchanged with the user regarding such sensor data, information exchanged with a remote site (e.g., a health care facility, emergency medical service, etc.), summaries of sensor data, baseline comparison data, etc.

For example, sub-step 1352 may comprise storing such information in a memory (e.g., a volatile and/or non-volatile memory device) that is integrated with the same garment in which the sensors are integrated and/or integrated in a different garment. Sub-step 1352 may comprise storing such information in a user's personal off-garment database and/or storing such information in a central healthcare database (e.g., associated with one or more health care providers).

Such stored information may, for example, be retained for later analysis and/or for later communication to another device. For example, sub-step 1352 may comprise storing such information in a memory that may be read by another device that is within personal area network wireless range of the memory. Also for example, sub-step 1352 may comprise storing such information in a memory that may be read by another device via a hardwire port (e.g., a USB and/or FireWire port).

Sub-step 1352 may, for example, comprise storing information in response to a determination made at sub-step 1351 to store such information. In a non-limiting exemplary scenario, sub-step 1351 may comprise determining that one or more particular monitored characteristics (e.g., physiological and/or non-physiological characteristics) should be stored for later analysis and/or monitored over a period of time. In such exemplary scenario, sub-step 1352 may comprise performing the information storage identified at sub-step 1351. Sub-step 1351 may also, for example, comprise storing information in response to receiving a request from a remote system (e.g., a health-care facility, a physician, an emergency response service, etc.) to acquire and/or store such information.

In general, sub-step 1232 comprises storing received sensor information (e.g., as received at step 1320) and/or analysis results information corresponding to such received sensor information (e.g., as determined at sub-step 1351). Accordingly, the scope of various aspects of the present invention should not be limited by any particular memory location or type, and/or by any particular manner of performing such information storage unless explicitly claimed.

Step 1350 may, for example at sub-step 1355, comprise interfacing with a user regarding sensor information and/or other related information. Sub-step 1355 may, for example, comprise performing such user interfacing in any of a variety of manners. Sub-step 1355 may, for example, share any or all characteristics with the exemplary sub-step 1255 of the exemplary method 1200 illustrated in FIG. 12 and discussed previously.

Step 1350 may, for example at sub-step 1356, comprise interfacing with a third party regarding sensor information and/or other related information (e.g., as received at step 1320, as analyzed at sub-step 1351 and/or as stored at step 1352). Sub-step 1356 may comprise performing such third-party interfacing in any of a variety of manners. Sub-step 1356 may, for example, share any or all characteristics with the exemplary sub-step 1256 of the exemplary method 1200 illustrated in FIG. 12 and discussed previously.

Step 1350 may, for example at sub-step 1358, comprise acquiring additional user health sensor information from the garment sensors (or other sensors) for additional analysis and/or communication. Sub-step 1358 may comprise performing such acquisition in any of a variety of manners. Sub-step 1358 may, for example, share any or all characteristics with the exemplary sub-step 1258 of the exemplary method 1200 illustrated in FIG. 12 and discussed previously.

Step 1350 may, for example at sub-step 1359, comprise acquiring additional user health information (e.g., from other sensors, from memory, etc.) for additional analysis and/or communication. Sub-step 1359 may comprise performing such acquisition in any of a variety of manners. Sub-step 1359 may, for example, share any or all characteristics with the exemplary sub-step 1259 of the exemplary method 1200 illustrated in FIG. 12 and discussed previously.

The exemplary method 1300 may, at step 1390, comprise performing continued operation. Such continued operation may comprise any of a variety of characteristics. For example, the characteristics of such continued operation may be determined based, at least in part, on the results of the analysis performed at step 1350. Various examples of such operation have already been presented. For example, step 1390 may comprise acquiring and/or analyzing additional physiological and/or non-physiological information, initiating and/or maintaining a communication with a third party, communication alert and/or instruction information with a user of a system implementing the method 1300 (e.g., the wearer of a garment in which the ECG sensors and/or the system implementing the method 1300 are integrated), etc.

The previous discussion of FIG. 13 focused primarily on monitoring, analyzing and/or communicating regarding information related to a plurality of different types of sensors (e.g., health-monitoring sensors) integrated in a garment worn by a user (or subject). It should be noted that the previous discussion of such sensors may be readily applied to a plurality of garments with any of a variety of different types of health-monitoring sensors integrated into the garments.

Figure 14:
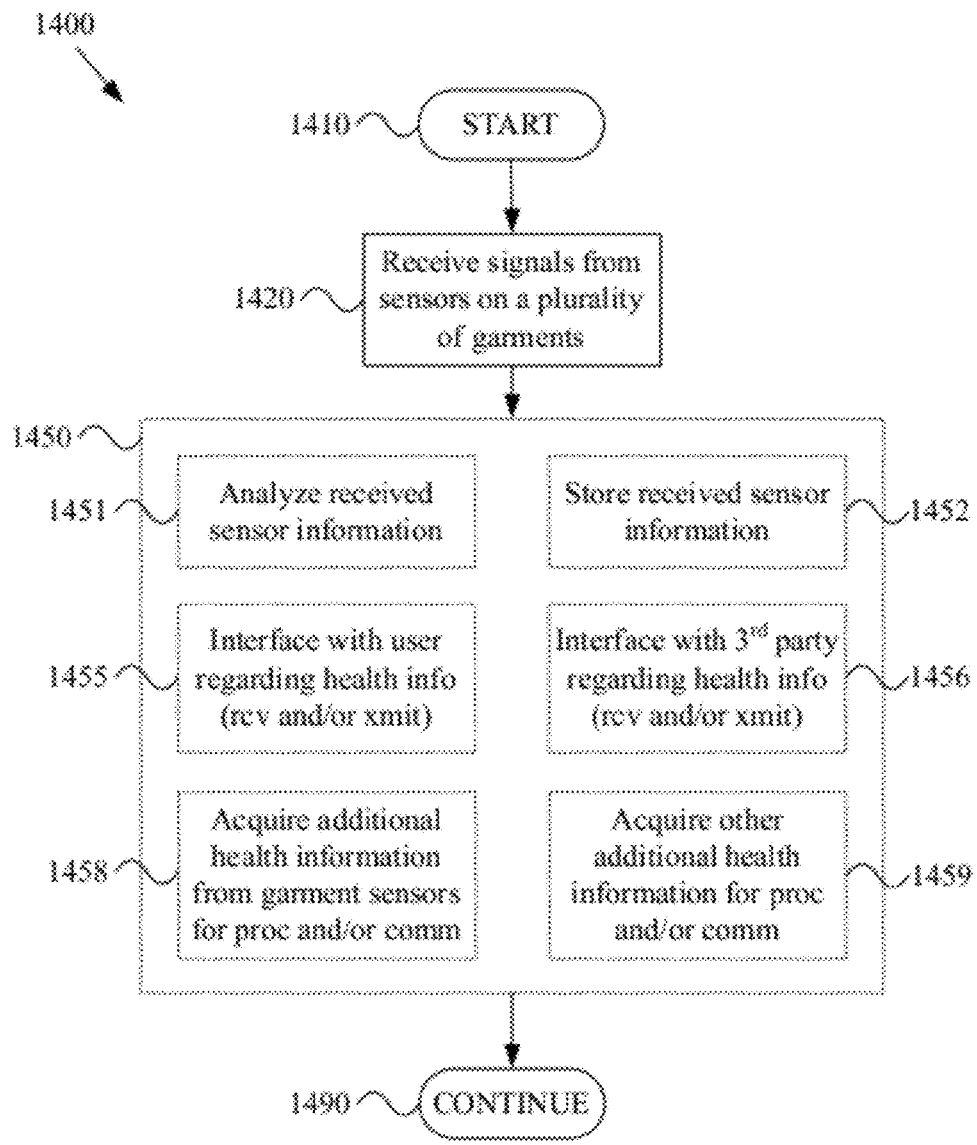
FIG. 14 is a flow diagram illustrating an exemplary method (e.g., in a garment system) for acquiring and/or processing health information of a user, in accordance with various aspects of the present invention.

Turning next to FIG. 14, such figure is a flow diagram 1400 illustrating an exemplary method (e.g., in a garment system) for acquiring and/or processing health information of a user, in accordance with various aspects of the present invention. While the previous discussion of FIG. 12 generally focused on cardiac (or ECG) sensors integrated into a garment (and the monitoring, analyzing and/or communicating associated therewith), and the discussion of FIG. 13 generally concerned a garment in which a plurality of different types of sensors were integrated (and the monitoring, analyzing and/or communicating associated therewith), the discussion of FIG. 14 will generally concern a garment system in which sensors (e.g., health-monitoring sensors) are integrated in a plurality of garments worn by the subject.

The exemplary method 1400 may begin executing at step 1410. The exemplary method 1400 may begin executing for any of a variety of causes and/or conditions. Such causes and/or conditions may, for example, share any or all characteristics with the causes and/or conditions discussed previously with regard to step 1210 of the exemplary method 1200 illustrated in FIG. 12.

The exemplary method 1400 may, at step 1420, comprise receiving signals from sensors integrated into a plurality of garments. Step 1420 may comprise receiving such signals in any of a variety of manners, non-limiting examples of which will now be provided. For example, step 1420 may share any or all characteristics with step 1320 of the exemplary method 1300 illustrated in FIG. 13 and discuss previously and with step 1220 of the exemplary method 1200 illustrated in FIG. 12 and discussed previously.

The previous discussion of FIGS. 1-11 provided many examples of sensors (e.g., both physiological and/or non-physiological sensors incorporated into a plurality of garments. Step 1420 may comprise receiving signals associated with any or all of such sensors. In general, when the following discussion discusses receiving and/or processing a sensor signal, such reference generally refers to any signal associated with a sensor. Such a signal may, for example, comprise a raw unprocessed signal from an electrode or other sensor, such a signal may comprise a data signal communicating digital data associated with a sensor reading or other sensor information, etc.

For example, step 1420 may comprise receiving sensor signals at a common location of a single garment. As illustrated in FIGS. 1-11, conductive paths (e.g., conductive fibers, conductive strips, etc.) may be formed into a garment to provide access to all sensors integrated into one or more garments at a single convenient location (e.g., a central location). In such a scenario, step 1420 may comprise receiving (e.g., with sensor-monitoring circuitry located at or near the central location) respective sensor signals associated with each of a plurality of sensors and integrated into a plurality of garments. As a non-limiting example, FIG. 5 shows a garment system 500 that couples ECG electrodes 531 and 532 of a second garment 502 to a central location of a first garment 501.

Additionally for example, step 1420 may comprise receiving one or more wireless signals communicating sensor reading information (e.g., wireless signal(s) describing one or more physiological and/or non-physiological characteristics measured at one or more respective sensors integrated into the garment, etc.). A non-limiting exemplary scenario comprising such wireless communication is shown at FIG. 8, which shows an impact sensor 881 and communication of information associated with such impact sensor 881 by a wireless RF communication device 882.

In such a wireless scenario, step 1420 may comprise receiving such wireless signal(s) communicated in accordance with any of a variety of standard and/or proprietary communication protocols (e.g., body area network protocols, personal area network protocols, local area network protocols, metropolitan area network protocols, cellular communication network protocols, satellite communication network protocols, Internet protocols, etc.). Such a protocol may, for example, comprise specific features (e.g. messages, message sequences, packet structures, packet fields, etc.) that are specifically adapted to the communication of sensor-specific information and/or other health-related information.

For example, step 1420 may comprise receiving the sensor signals separately, combined into a single data structure or packet, combined with signals associated with other physiological and/or non-physiological sensors, etc. For example, step 1420 may comprise receiving the sensor signals at a device integrated with one or more of the plurality of garments. Also for example, as exemplified at FIGS. 10 and 11, step 1420 may comprise receiving the sensor signals at a device separate from the garment(s) but worn by (or positioned near) the user. Additionally, as exemplified at FIG. 11 (e.g., via a communication link 1196), step 1420 may comprise receiving the sensor signals at a location remote from the user (e.g., at user equipment at a remote premises, at a health care facility, at an emergency vehicle, at a doctor's cellular telephone, etc.).

In general, step 1420 may comprise receiving signals from sensors integrated into a plurality of garments. Accordingly, the scope of various aspects of the present invention should not be limited by characteristics of any particular manner of receiving such signals or by characteristics of any particular type of signal and/or sensor unless explicitly claimed.

The exemplary method 1400 may, at step 1450, comprise analyzing the sensor signals (e.g., sensor signals received at step 1420) to ascertain the health (e.g., the cardiovascular health) of the garment wearer. Step 1450 may comprise analyzing the sensor signals in any of a variety of manners, non-limiting examples of which will now be provided. Step 1450 may, for example, share any or all characteristics with step 1350 of the exemplary method 1300 illustrated in FIG. 13 and discussed previously and with step 1250 of the exemplary method 1200 illustrated in FIG. 12 and discussed previously.

Step 1450 will now be exemplified by various different types of analysis that may be performed. The following discussion of step 1450 is divided into non-limiting exemplary sub-steps for the sake of illustrative clarity. Step 1450 may, for example, comprise any or all characteristics of such exemplary sub-steps.

Step 1450 may, for example at sub-step 1451, comprise analyzing received sensor information. Such analysis may, for example, comprise analyzing the received sensor information in light of various pathologies (e.g., in light of various cardiac pathologies). Sub-step 1451 may, for example, share any or all characteristics with the exemplary sub-step 1351 of the method 1300 illustrated in FIG. 13 and discussed previously and exemplary sub-step 1251 of the method 1200 illustrated in FIG. 12 and discussed previously.

The previous discussion of sub-step 1251 generally focused on ECG sensor analysis, and the previous discussion of sub-step 1351 generally focused on different types of sensors integrated into a single garment. Such analysis techniques are also applicable to other types of sensor analysis (e.g., analysis involving sensors integrated into a plurality of garments). Sub-step 1451 may be viewed as adding garment flexibility to the analysis discussed with regard to sub-steps 1351 and 1251. For example, though sub-step 1251 generally concerned cardiac (or ECG) sensors integrated into a single garment, sub-step 1451 broadens such scenario to one in which the cardiac (or ECG) sensors may be integrated into a plurality of garments (e.g., as exemplified in a non-limiting manner at FIG. 5). Also for example, though sub-step 1351 generally concerned different types of sensor integrated into a single garment, sub-step 1451 broadens such scenario to one in which the different types of sensors may be integrated into a plurality of garments (e.g., as exemplified in a non-limiting manner at FIG. 8).

As with sub-step 1351, the exemplary sub-step 1451 provides the capability to analyze physiological sensor signals in an environmental and/or situational (or activity) context. As with sub-step 1251, the exemplary sub-step 1451 provides the capability to analyze ECG information (e.g., performing a 12-lead ECG analysis), albeit utilizing ECG electrodes integrated into a plurality of garments.

Sub-step 1451 may, for example, be performed by one or more processors. Such processor(s) may, for example, be integrated in one or more of the same garments as the garments in which the sensors are integrated, and/or may be integrated in a different garment. Such processor(s) may also, for example, be located in a device (e.g., a personal electronic device) separate from the garments. Additionally, such processor(s) may be located at a premises (e.g., at a user's personal computing system, at a health-care provider's facility, in an emergency vehicle, etc.).

In general sub-step 1451 may comprise analyzing sensor signals (e.g., sensor signals received at step 1420) to ascertain the health of the garment wearer. Accordingly, the scope of various aspects of the present invention should not be limited by characteristics of particular types of sensor signals and/or characteristics of any particular manner of processing such signals unless explicitly claimed.

Step 1450 may, for example at sub-step 1452, comprise storing received sensor information (e.g., as received at step 1420) and/or analysis results information corresponding to such received cardiac information (e.g., as determined at sub-step 1451). Sub-step 1452 may comprise performing such storage in any of a variety of manners, non-limiting examples of which will now be presented.

The stored information may, for example, include raw sensor data, the results of processed sensor data, information exchanged with the user regarding such sensor data, information exchanged with a remote site (e.g., a health care facility, emergency medical service, etc.), summaries of sensor data, baseline comparison data, etc.

For example, sub-step 1452 may comprise storing such information in a memory (e.g., a volatile and/or non-volatile memory device) that is integrated with the same garment(s) in which the sensors are integrated and/or integrated in a different garment. In an exemplary scenario, a memory on a first garment may be utilized to store information pertaining to sensors that are integrated into a plurality of garments. Sub-step 1452 may comprise storing such information in a user's personal off-garment database and/or storing such information in a central healthcare database (e.g., associated with one or more health care providers).

Such stored information may, for example, be retained for later analysis and/or for later communication to another device. For example, sub-step 1452 may comprise storing such information in a memory that may be read by another device that is within personal area network wireless range of the memory. Also for example, sub-step 1452 may comprise storing such information in a memory that may be read by another device via a hardwire port (e.g., a USB and/or FireWire port).

Sub-step 1452 may, for example, comprise storing information in response to a determination made at sub-step 1451 to store such information. In a non-limiting exemplary scenario, sub-step 1451 may comprise determining that one or more particular monitored characteristics (e.g., physiological and/or non-physiological characteristics) should be stored for later analysis and/or monitored over a period of time. In such exemplary scenario, sub-step 1452 may comprise performing the information storage identified at sub-step 1451. Sub-step 1451 may also, for example, comprise storing information in response to receiving a request from a remote system (e.g., a health-care facility, a physician, an emergency response service, etc.) to acquire and/or store such information.

In general, sub-step 1452 comprises storing received sensor information (e.g., as received at step 1420) and/or analysis results information corresponding to such received sensor information (e.g., as determined at sub-step 1451). Accordingly, the scope of various aspects of the present invention should not be limited by any particular memory location or type, and/or by any particular manner of performing such information storage unless explicitly claimed.

Step 1450 may, for example at sub-step 1455, comprise interfacing with a user regarding sensor information and/or other related information. Sub-step 1455 may, for example, comprise performing such user interfacing in any of a variety of manners. Sub-step 1455 may, for example, share any or all characteristics with the exemplary sub-steps 1255 and 1355 of the exemplary methods 1200 and 1300 illustrated in FIGS. 12-13 and discussed previously.

Step 1450 may, for example at sub-step 1456, comprise interfacing with a third party regarding sensor information and/or other related information (e.g., as received at step 1420, as analyzed at sub-step 1451 and/or as stored at step 1452). Sub-step 1456 may comprise performing such third-party interfacing in any of a variety of manners. Sub-step 1456 may, for example, share any or all characteristics with the exemplary sub-steps 1256 and 1356 of the exemplary methods 1200 and 1300 illustrated in FIGS. 12-13 and discussed previously.

Step 1450 may, for example at sub-step 1458, comprise acquiring additional user health sensor information from the garment sensors (or other sensors) for additional analysis and/or communication. Sub-step 1458 may comprise performing such acquisition in any of a variety of manners. Sub-step 1458 may, for example, share any or all characteristics with the exemplary sub-steps 1258 and 1358 of the exemplary methods 1200 and 1300 illustrated in FIGS. 12-13 and discussed previously.

Step 1450 may, for example at sub-step 1459, comprise acquiring additional user health information (e.g., from other sensors, from memory, etc.) for additional analysis and/or communication. Sub-step 1459 may comprise performing such acquisition in any of a variety of manners. Sub-step 1459 may, for example, share any or all characteristics with the exemplary sub-steps 1259 and 1359 of the exemplary methods 1200 and 1300 illustrated in FIGS. 12-13 and discussed previously.

The exemplary method 1400 may, at step 1490, comprise performing continued operation. Such continued operation may comprise any of a variety of characteristics. For example, the characteristics of such continued operation may be determined based, at least in part, on the results of the analysis performed at step 1450. Various examples of such operation have already been presented. For example, step 1490 may comprise acquiring and/or analyzing additional physiological and/or non-physiological information, initiating and/or maintaining a communication with a third party, communication alert and/or instruction information with a user of a system implementing the method 1400 (e.g., the wearer of a garment in which the ECG sensors and/or the system implementing the method 1400 are integrated), etc.

The previous discussion of FIGS. 12-14 provided various non-limiting examples of garment-integrated sensor monitoring, analyzing and/or communicating. It should be noted that such examples were for illustrative purposes only and were not meant to be limiting. Accordingly, the scope of various aspects of the present invention should not be limited by characteristics of any of such examples unless explicitly claimed.

Figure 15:
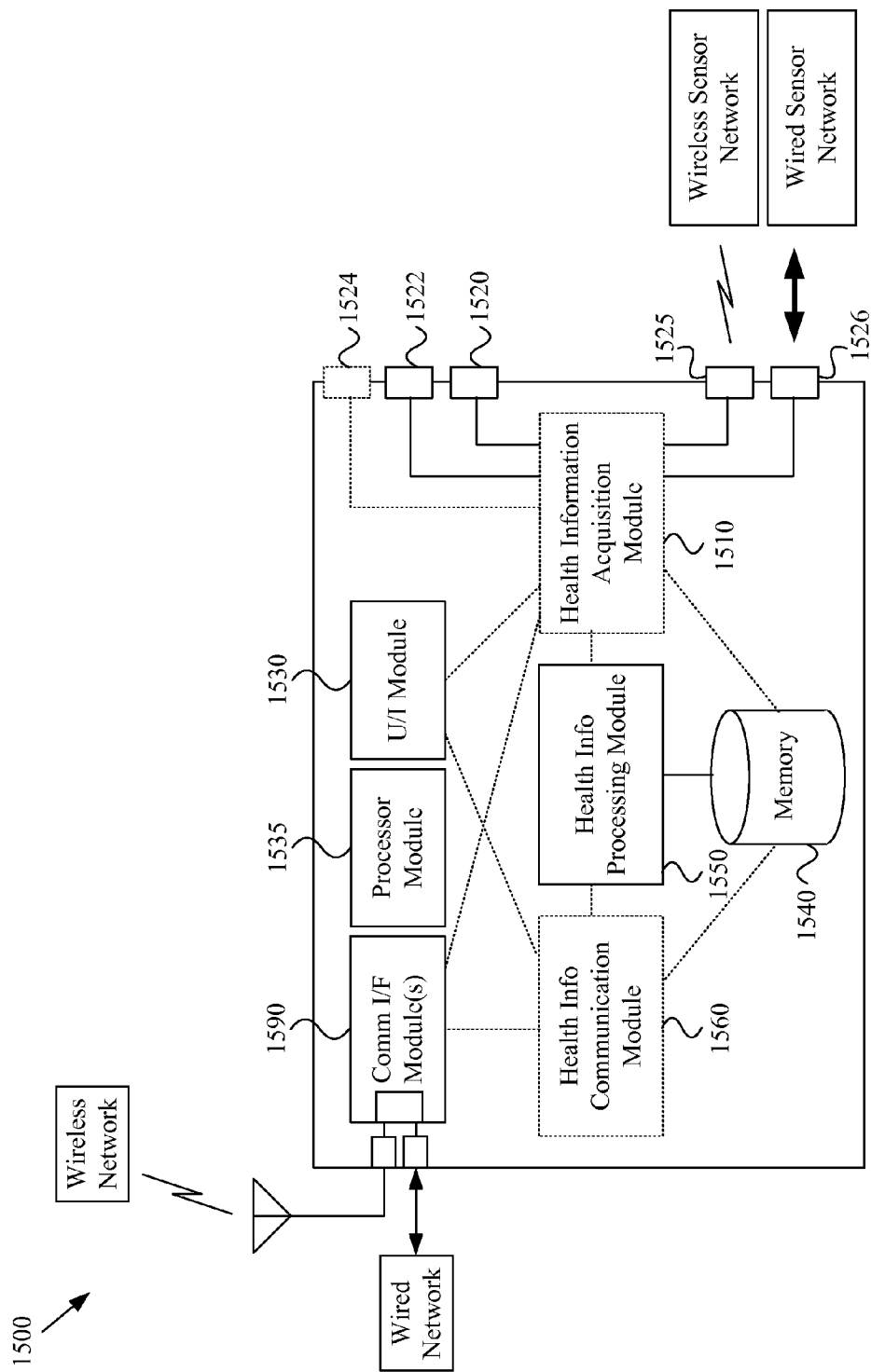
FIG. 15 is a block diagram illustrating an exemplary processing system operable to acquire and/or process health information (e.g., in a garment system), in accordance with various aspects of the present invention.

FIG. 15 is a block diagram illustrating an exemplary processing system 1500 operable to acquire and/or process health information (e.g., in a garment system), in accordance with various aspects of the present invention. The exemplary system 1500 (or one or more modules thereof) may, for example, operate to perform any or all of the exemplary functionality discussed with regard to FIGS. 1-14.

The exemplary system 1500 may, for example, be implemented in a single device. Such a single device may, for example, be integrated into a garment (e.g., the same one or more garments in which the sensors of interest are integrated). Also for example, such a single device may be a stand-alone dedicated personal health-monitoring device. Additionally for example, such a single device may be a personal electronic device (e.g., a cellular telephone, a personal digital assistant, a handheld computer, a portable email device, a portable music playing device, etc.). Further for example, such a single device may be a personal computer system (e.g., a desktop computer system, a laptop or notebook computer system, a handheld computer system, etc.). Still further for example, such a single device may be a centralized computing device (e.g., located at a health-care facility, emergency service center, emergency vehicle, physician office, etc.).

The exemplary system 1500 may also, for example, be implemented in a distributed system (e.g., with dispersed components). In other words, the various components and/or modules of the system 1500 might not be co-located in a single electrical device. For example, various modules of the system 1500 may be integrated in a plurality of different garments. Also for example, a first set of modules of the system 1500 may be integrated in a garment (e.g., sensor information acquisition modules and communication modules), and a second set of modules of the system 1500 may be implemented in a personal electronic device (e.g., information processing modules and/or other communication modules). Additionally for example, a first set of modules of the system 1500 may be integrated in a garment (e.g., sensor information acquisition modules and communication modules), and a second set of modules of the system 1500 may be implemented in a personal computing system (e.g., information processing modules and/or other communication modules).

Additionally for example, a first set of modules of the system 1500 may be integrated in a garment (e.g., sensor information acquisition modules and communication modules), and a second set of modules of the system 1500 may be implemented in a centralized system (e.g., information processing modules and/or other communication modules). Further for example, a first set of modules of the system 1500 may be integrated in a garment (e.g., sensor information acquisition modules and communication modules), a second set of modules of the system 1500 may be implemented in a personal electronic device (e.g., information processing modules and/or other communication modules), and a third set of modules of the system 1500 may be implemented in a centralized computing system (e.g., other information processing modules and/or still other communication modules).

The following discussion will generally present the exemplary system 1500 as being implemented in a personal electronic device (e.g., communicatively couplable to one or more garments comprising integrated sensors and/or communicatively couplable to one or more centralized computing systems). Note, however, that the scope of various aspects of the present invention should not be limited to specific implementation characteristics of the exemplary system 1500 (e.g., the location of the system 1500 and/or modules thereof) unless explicitly claimed.

The exemplary system 1500 may, for example, comprise a plurality of sensor communication ports 1520, 1522, 1524, 1525 and 1526 via which the system 1500 may communicate with a plurality of sensors. For example, the exemplary system 1500 comprises a health information acquisition module 1510 that operates to acquire sensor signals and/or information from sensors integrated into garments and/or other sensors. The health information acquisition module 1510 may (e.g., via the communication ports) operate to perform any or all of the functionality discussed previously with regard to the acquisition of signals and/or information from various sensors. For example and without limitation, the health information acquisition module 1510 may operate to perform functionality associated with steps 1220, 1258 and 1259 of FIG. 12; steps 1320, 1328 and 1329 of FIG. 13; and/or steps 1420, 1428 and 1429 of FIG. 14.

The manner in which the health information acquisition module acquires such signals and/or information depends on the type of sensor from which such signals and/or information is obtained. For example, in various scenarios discussed previously, the health information acquisition module 1510 may operate to receive a raw unprocessed analog signal from a sensor (e.g., an analog voltage signal from an electrode). In other exemplary scenarios, for example, the health information acquisition module 1510 may operate to receive one or more signals from a sensor communicating data from such sensor.

The exemplary system 1500 may, for example, comprise one or more communication interface modules 1590 via which the system 1500 may communicate with a plurality of other systems utilizing wired and/or wireless communication. The health information acquisition module 1510 may (e.g., via the communication interface modules 1590) operate to perform any or all of the functionality discussed previously with regard to the acquisition of non-sensor health-related information. For example and without limitation, the health information acquisition module 1510 may operate to perform functionality associated with step 1259 of FIG. 12, step 1329 of FIG. 13, and/or step 1429 of FIG. 14.

The manner in which the health information acquisition module acquires such non-sensor information depends on the nature of the source from which such information is obtained and/or the nature of the communication network(s) communicatively coupling the system 1500 to such source. For example, in various scenarios discussed previously, the health information acquisition module 1510 may operate to receive such information from a wired and/or wireless data communication network, a wired and/or wireless telecommunication network, a wired and/or wireless television communication network, etc.

The exemplary system 1500 comprises a health information processing module 1550. Such processing module 1550 may, for example, comprise hardware and/or a combination of hardware and operating instructions that operate to perform any or all of the information processing functionality discussed herein. For example, the health information processing module 1550 may operate to perform any or all of the analysis functionality discussed previously with regard to steps 1250 and 1251 of FIG. 12, steps 1350 and 1351 of FIG. 13, and/or steps 1450 and 1451 of FIG. 14.

The exemplary system 1500 also comprises a memory 1540. Such memory 1540 may, for example, operate to store processor operating instructions, sensor analysis results, sensor data, user information, contact information, user instruction information, etc. Such memory 1540 may, for example, be utilized to perform any or all of the information storage functionality discussed here (e.g., with regard to steps 1252, 1352 and 1452 of FIGS. 12-14).

The exemplary system 1500 additionally comprises one or more user interface modules 1530. Such user interface module(s) 1530 may, for example, operate to communicate information with a user (e.g., receive input information from such user and/or output information to such user). For example, the exemplary system 1500 (e.g., a processing module thereof) may operate to utilize the user interface module(s) 1530 to implement any or all of the user interface functionality discussed herein (e.g., with regard to steps 1255, 1355 and 1455 of FIGS. 12-14).

The exemplary system 1500 further comprises a health information communication module 1560. Such health information communication module 1560 may, for example, operate to communication health information with an external system (e.g., a third party computing system, a user computing system, etc.). For example, the health information communication module 1560 may operate to utilize one or more of the communication interface modules 1590 to perform such communication. The health information communication module 1560 may, for example, operate to utilize the communication interface module(s) 1590 to implement any or all of the health information communication functionality discussed herein (e.g., with regard to steps 1256 and 1259 of FIG. 12, steps 1356 and 1359 of FIG. 13, and steps 1456 and 1459 of FIG. 14).

The exemplary system 1500 comprises a processor module 1535 and a memory 1540. As explained previously, the various modules of the system 1500 may, for example, be implemented in hardware or a combination of hardware and software. In an exemplary scenario, the system 1500 comprises a processor module 1535 and memory 1540, which may, for example, be utilized to implement any or all portions of the previously discussed modules.

Though not illustrated in FIG. 15, the exemplary system 1500 may receive electrical power from any of a variety of sources. For example, in a scenario where at least one module of the exemplary system 1500 is integrated into a garment (e.g., one or more of garments in which sensors are integrated), a power supply for such at least one module may be integrated into the garment and/or a power supply connection may be integrated into such garment via which power may be supplied to such at least one module by a source external to such garment. Also for example, in a scenario where at least one module of the exemplary system 1500 is integrated into a personal electronic device (e.g., a cellular telephone, personal computing device, etc.), a power supply for such at least one module may located in such personal electronic device. Additionally, in a scenario where at least one module of the exemplary system 1500 is integrated into a garment (e.g., one or more of garments in which sensors are integrated) and at least one module of the exemplary system 1500 is integrated into a personal electronic device, such system may comprise independent power supplies (e.g., a power supply integrated with such garment and a power supply of the personal electronic device) or may comprise a single power supply (e.g., a power supply of the personal electronic device) that is shared between the garment and the personal electronic device.

Figure 16:
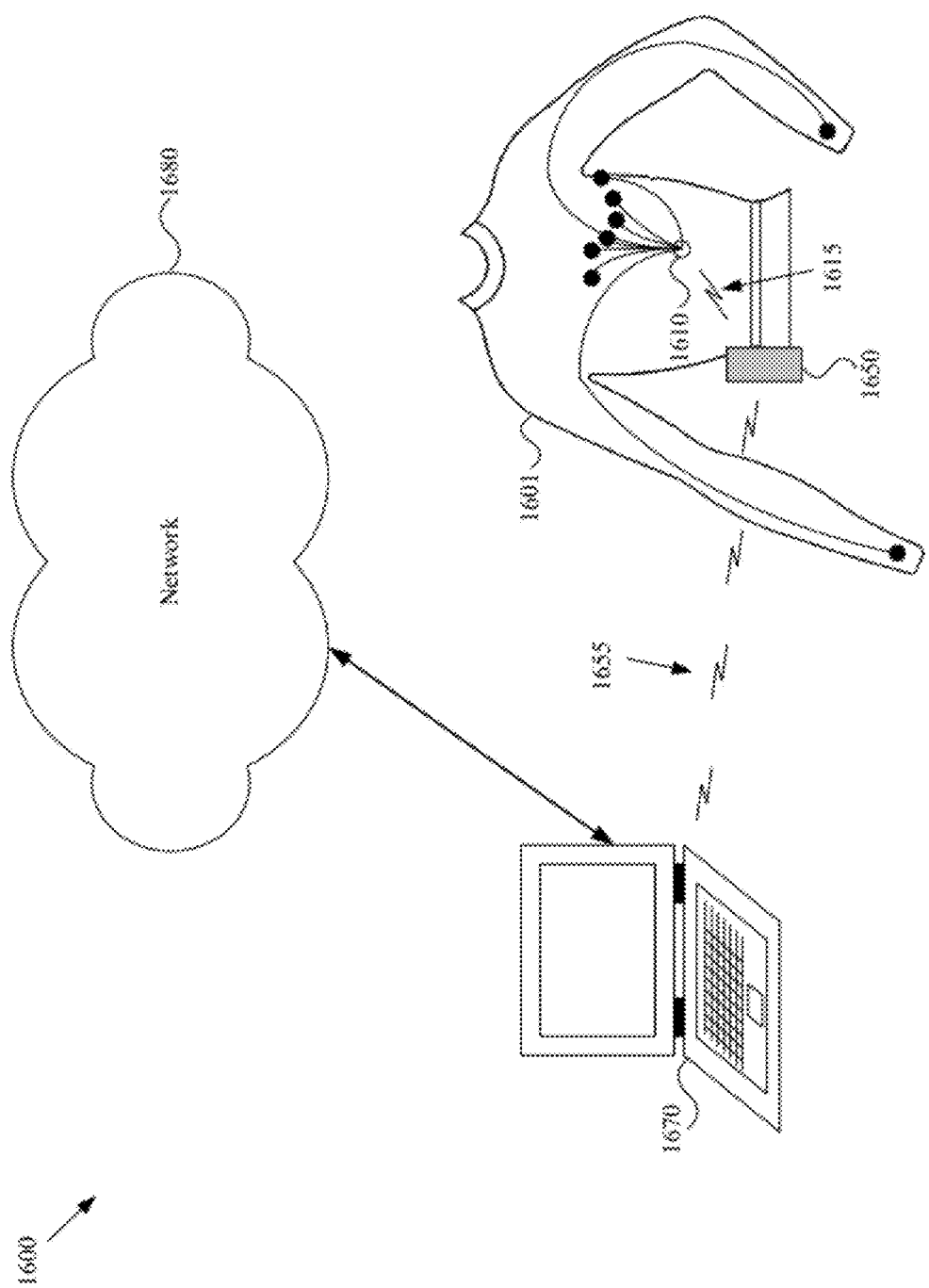
FIG. 16 is a diagram illustrating an exemplary health analysis system, in accordance with various aspects of the present invention.
Figure 17:
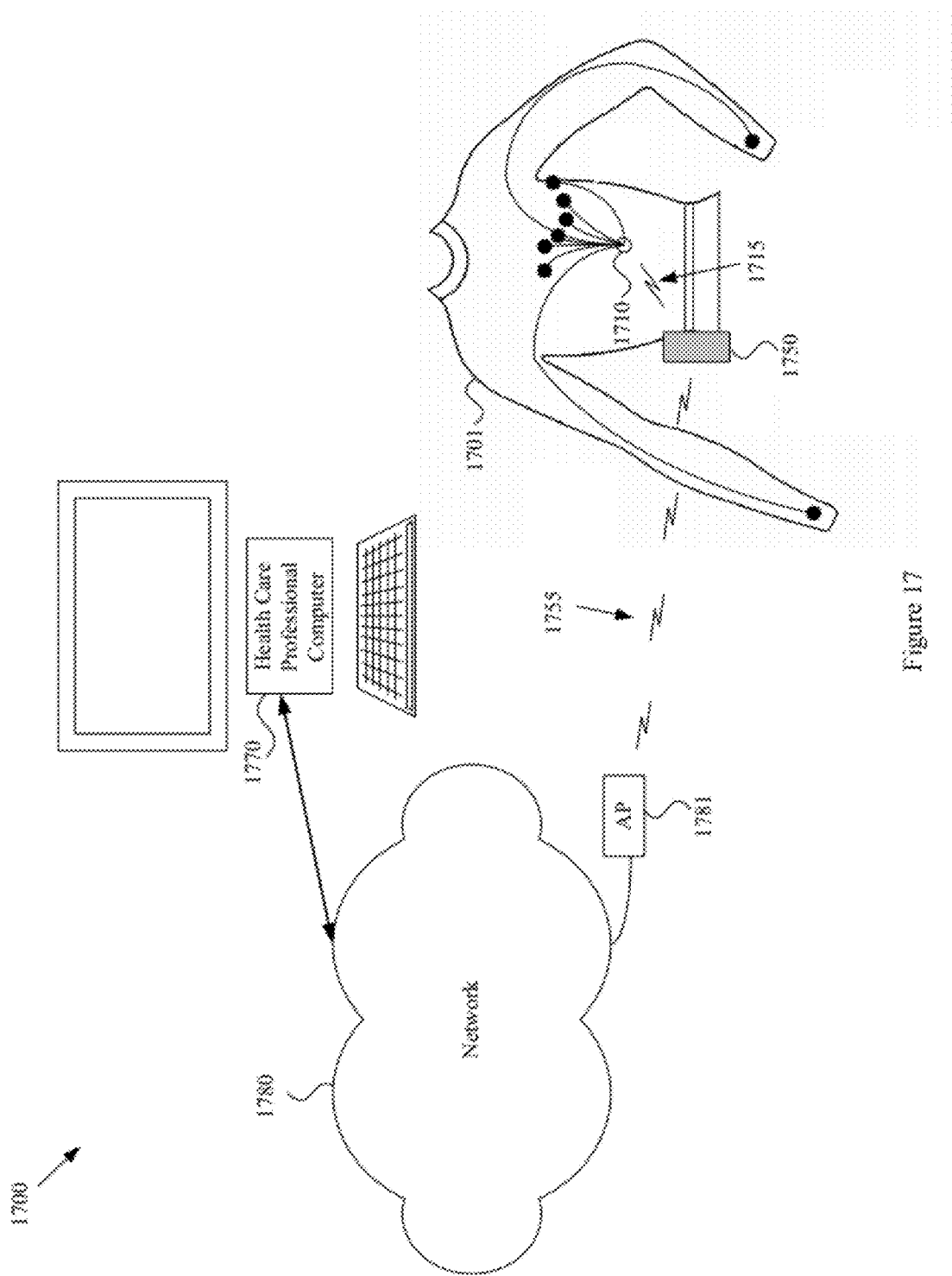
FIG. 17 is a diagram illustrating an exemplary health analysis system, in accordance with various aspects of the present invention.

As mentioned above, a health analysis system in accordance with various aspects of the present invention may be implemented in any of a variety of system configurations. Aspects of many of such configurations were discussed previously. FIGS. 16 and 17 provide additional system configuration examples.

FIG. 16 is a diagram illustrating an exemplary health analysis system 1600, in accordance with various aspects of the present invention. The exemplary system 1600 may, for example, comprise a garment 1601 comprising integrated cardiac (e.g., ECG) sensors that are conductively coupled to a central location 1610 of the garment 1601 for convenient access. In the exemplary system 1600, a low-power transceiver (e.g., a personal area network and/or body area network transceiver) is also integrated into the garment 1601 at the central location 1610. Circuitry at the central location 1610 operates to receive ECG signals from the various in-garment electrodes, prepare information describing such signals for transmission (e.g., characterizing such signals in terms of a set of voltage potential differences), and utilize a low-power transceiver to transmit ECG information to a personal electronic device 1650 worn by the user (e.g., in a belt holster). The personal electronic device 1650 then, for example, operates as a medium-power transceiver, transmitting the ECG information to a laptop computer 1670, which then analyzes the ECG information. The laptop computer 1670 then communicates analysis results to other entities (e.g., to third parties, for example, health care providers, emergency services personnel, etc.) via a communication network 1680.

The exemplary system 1600 may implement the various FIG. 15 modules in any of a variety of system components. For example, in a first exemplary configuration, the laptop computer 1670 might share any or all characteristics with the exemplary system 1500 of FIG. 15. In such a scenario, the electronics at the central location 1610 might implement only a portion of the functionality of the Health Information Acquisition Module 1510 of the system 1500 of FIG. 15 (e.g., functionality concerning the acquisition of ECG sensor signals and preparing information descriptive of such signals for communication). Also, in such a scenario, the personal electronic device 1650 might implement only a portion of the functionality of the Health Information Acquisition Module 1510 and U/I Module 1530 of the system 1500 of FIG. 15 (e.g., functionality concerning the receipt and forwarding of sensor information to the laptop computer 1670 for processing).

In another exemplary configuration, the personal electronic device 1650 may share any or all characteristics with the exemplary system 1500 of FIG. 15. In such a scenario, the electronics at the central location 1610 might implement only a portion of the functionality of the Health Information Acquisition Module 1510 of the system 1500 of FIG. 15 (e.g., functionality concerning the acquisition of ECG sensor signals and preparing information descriptive of such signals for communication). Also for example, in such a scenario, the personal laptop computer 1670 might implement only a portion of the Communication Interface Module(s) 1590 of the system 1500 of FIG. 15 (e.g., functionality concerning communication with a third party via a communication network 1680).

FIG. 17 is a diagram illustrating an exemplary health analysis system 1700, in accordance with various aspects of the present invention. The exemplary system 1700 may, for example, comprise a garment 1701 comprising integrated cardiac (e.g., ECG) sensors that are conductively coupled to a central location 1710 of the garment 1701 for convenient access. In the exemplary system 1700, a low-power transceiver (e.g., a personal area network and/or body area network transceiver) is also integrated into the garment 1701 at the central location 1710. Circuitry at the central location 1710 operates to receive ECG signals from the various in-garment electrodes, prepare information describing such signals for transmission (e.g., characterizing such signals in terms of a set of voltage potential differences), and utilize a low-power transceiver to transmit ECG information to a personal electronic device 1750 worn by the user (e.g., in a belt holster). The personal electronic device 1750 then, for example, operates as a high-power transceiver, transmitting the ECG information to a central system 1770 (e.g., a computer system of a health care facility, physician, emergency technician, etc.) via a wireless communication link 1755, a communication network access point 1781 (e.g., a cellular base station, wireless LAN access point, etc.), and a communication network 1780 (e.g., cellular infrastructure, Internet, etc.), which then analyzes the ECG information. The central computing system 1770 then communicates analysis results to other entities if necessary and/or communicates information back to the wearer of the garment 1701.

The exemplary system 1700 may implement the various FIG. 15 modules in any of a variety of system components. For example, in a first exemplary configuration, the central computer system 1770 might share any or all characteristics with the exemplary system 1500 of FIG. 15. In such a scenario, the electronics at the central location 1710 of the garment 1701 might implement only a portion of the functionality of the Health Information Acquisition Module 1510 of the system 1500 of FIG. 15 (e.g., functionality concerning the acquisition of ECG sensor signals and preparing information descriptive of such signals for communication). Also, in such a scenario, the personal electronic device 1750 might implement only a portion of the functionality of the Health Information Acquisition Module 1510 and U/I Module 1530 of the system 1500 of FIG. 15 (e.g., functionality concerning the receipt and forwarding of sensor information to the central computer system 1770 for processing).

In another exemplary configuration, the personal electronic device 1750 may share any or all characteristics with the exemplary system 1500 of FIG. 15. In such a scenario, the electronics at the central location 1710 of the garment 1701 might implement only a portion of the functionality of the Health Information Acquisition Module 1510 of the system 1500 of FIG. 15 (e.g., functionality concerning the acquisition of ECG sensor signals and preparing information descriptive of such signals for communication). Also for example, in such a scenario, the central computer system 1770 might merely operate as a recipient of sensor and/or analysis results from the personal electronic device 1750.

Figure 18:
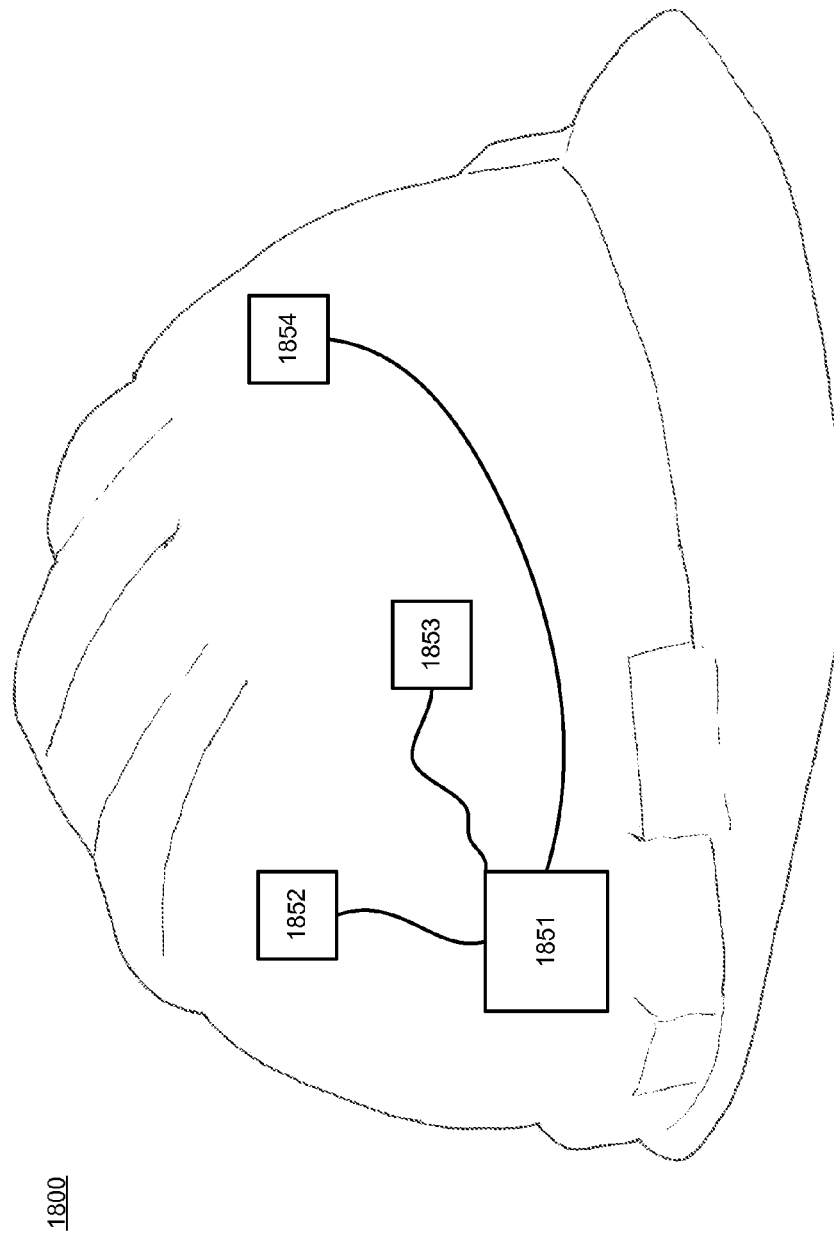
FIG. 18 is a diagram illustrating an exemplary garment (e.g., hard hat) health-monitoring system, in accordance with various aspects of the present invention.

FIG. 18 is a diagram illustrating an exemplary garment (e.g., hard hat) health-monitoring system 1800, in accordance with various aspects of the present invention. As shown in FIG. 18, the system 1800 includes a processing system 1851 that may correspond to, for example, the processing system 1500, described above with respect to FIG. 15. The system 1800 also includes sensors 1852, 1853, 1854, each of which are coupled to the processing system 1851, and each of which may be, for example, a physiological or non-physiological (e.g., environmental and/or situational) sensor, as described above. It should be noted that although FIG. 18 shows three sensors 1852, 1853, 1854, a representative embodiment of the present invention may employ a greater or lesser number of sensors without departing from the spirit and scope of the present invention. Each physiological sensor of the sensors 1852, 1853, 1854 may be, for example, a physiological sensor that operates to monitor physiological characteristics of a person (or subject). Such physiological sensors may, for example and without limitation, comprise a heart monitoring sensor (e.g., heart-rate monitoring sensors, electrocardiogram (ECG or EKG) sensors), a body temperature sensor, breath-rate/respiration sensor (e.g., pressure-based (e.g., material stress, air pressure/bladder, etc.), or an acoustic-based sensor, etc.), a skin conductivity sensor, an oxygen saturation sensor, or a blood perfusion sensor. Each non-physiological sensor of the sensors 1852, 1853, 1854 may be, for example, an environmental sensor such as one of an air temperature sensor, an air speed sensor, a humidity sensors, an air oxygen level sensor, a barometric pressure sensor, an altitude/elevation sensor, a precipitation sensor, a light sensor, a location sensors/systems (e.g., global positioning system (GPS) sensor, a terrestrial triangulation sensor/system (e.g., cellular communication system based, premises based, campus based, etc.)), a time sensor (e.g., time change and/or absolute time), and/or an orientation sensor. Each non-physiological sensor of the sensors 1852, 1853, 1854 may be, for example, a situational sensor that operates to monitor characteristics of a physical situation (e.g., a task or activity) in which the subject is engaged. Such a situational (or activity) sensor may, for example and without limitation, comprise a weight sensor, an impact sensor, a force sensor, a pressure sensor, an accelerometer, an inclinometer, a motion sensor, and/or a speed and/or velocity sensor.

In summary, various aspects of the present invention provide a garment and/or garment system with health-monitoring (e.g., cardiovascular monitoring) capability.

Various aspects of the present invention may be implemented in various degrees of integration. For example, various modules may be integrated in an independent integrated circuit or may be integrated into other integrated circuits. For example and without limitation, various modules discussed herein may be integrated into a baseband processor chip or controller chip. Accordingly, the scope of various aspects of the present invention should not be limited by characteristics of any particular degree of integration.

Various aspects of the present invention were illustrated by referring to various functional modules. It should be noted that such modules may be implemented in hardware or a combination of hardware and software. Additionally, various modules may share various submodules or subcomponents. For example, a first module and a second module may share a particular hardware component or software submodule. Accordingly, the scope of various aspects of the present invention should not be limited by characteristics of any particular type of module or by any arbitrary boundary between modules.

Further, various functional modules have been described herein utilizing the terminology "operate to" when referring to functionality that the various functional modules might perform when operational. Thus, the phrase "operate to", as used herein, is generally synonymous with "capable of", "operational to", "adapted to" and "configured to".

While the invention has been described with reference to certain aspects and embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. A garment comprising: a plurality of electrocardiogram (ECG) sensors configured to receive physiological signals from a user wearing said garment; one or more non-physiological sensors configured to detect one or more characteristics of air surrounding the user; one or more processors communicatively coupled to the plurality of ECG sensors and the one or more non-physiological sensors; at least one interface that operates to provide communication between said one or more processors and said plurality of ECG sensors and between said one or more processors and said one or more physiological sensors; and wherein said one or more processors are configured to begin processing of signals from said ECG sensors in response to detection, by said one or more processors, of at least one particular characteristic of said air surrounding said user, based on signals from said one or more non-physiological sensors.

2. The garment of claim 1, where said garment comprises a shirt.

3. The garment of claim 1, where said garment comprises one or more of: a pair of pants, a pair of shorts, a sock, a swim suit, a body suit, a hat, and a glove.

4. The garment of claim 1, wherein said plurality of ECG sensors each comprise respective conductive fiber woven into the garment.

5. The garment of claim 1, where the one or more processors are part of a general-purpose personal communication device.

6. The garment of claim 1, where the one or more processors are part of a general-purpose personal computer system.

7. The garment of claim 1, where the one or more processors are part of a health care enterprise computer system.

8. A system for ascertaining health of a wearer of a garment, the system comprising:
at least one module operable to, at least:
receive a plurality of signals from a respective plurality of electrocardiogram (ECG) sensors configured to receive physiological signals from a wearer of said garment;
receive one or more non-physiological signals from corresponding sensors configured to detect one or more characteristics of air surrounding said garment; and
one or more processors configured to initiate analysis of at least the received plurality of signals from said plurality of ECG sensors, in response to detection of at least one particular characteristic of said air surrounding said user, based upon signals from said one or more non-physiological sensors, to ascertain cardiovascular health of the wearer of the garment.

9. The system of claim 8, wherein at least a portion of said at least one module is integrated into the garment.

10. The system of claim 8, wherein said at least one module comprises at least one module of a general purpose personal communication device.

11. The system of claim 8, wherein said at least one module comprises at least one module of a general purpose personal computer system.

12. The system of claim 8, wherein said at least one module comprises at least one module of a health-care enterprise computer system.

13. A garment system comprising: a user garment comprising: a first sensor configured to detect a first physiological characteristic of a user wearing said garment, a second sensor configured to detect a second non-physiological characteristic of air surrounding said garment, and an interface that operates to communicate signals from said first sensor and said second sensor to a personal electronic device located with said user, wherein said personal electronic device is separate from said garment; and a computer application configured for execution on one or more processors of said personal electronic device, wherein said computer application is configured to initiate processing of signals from said first sensor, in response to detection, by said one or more processors, of at least one particular characteristic of said air surrounding said garment, based upon signals from said second sensor.

14. The garment system of claim 13, wherein the first sensor comprises an ECG electrode.

15. The garment system of claim 13, wherein the second sensor comprises one of an air temperature sensor and an air humidity sensor.

16. The garment system of claim 15, wherein said at least one particular characteristic of said air comprises one of a change in temperature and a change of humidity of said air surrounding said garment.

17. The garment system of claim 13, where said garment comprises a shirt.

18. The garment system of claim 13, where said garment comprises one or more of: a pair of pants, a pair of shorts, a sock, a swim suit, a body suit, a hat, and a glove.

19. The garment system of claim 13, wherein said interface is configured to communicate with said personal electronic device via a wireless interface for a personal area network.

20. The garment system of claim 13, wherein the garment comprises one or more processors.

21. The garment system of claim 13, where the personal electronic device is a general-purpose personal communication device configured for use on a public wireless network.

22. The garment system of claim 21, wherein said computer application of said personal electronic device communicates sensor information to a general-purpose personal computer system via the public wireless network.

23. The garment system of claim 21, wherein said computer application of said personal electronic device communicates with a health care enterprise computer system.

24. A system for ascertaining health of a wearer of a garment, the system comprising:
   at least one module operable to, at least:
      receive a first signal corresponding to a first sensor of a garment comprising a plurality of sensors, the first sensor of a physiological type of sensor;
      receive a second signal corresponding to a second sensor of the garment, the second sensor comprising a non-physiological type of sensor configured to detect one or more characteristics of air surrounding said wearer of said garment; and
      initiate analysis of at least the received first signal, in response to detection of at least one particular characteristic of said air surrounding said garment, based upon signals from said one or more non-physiological sensors, to ascertain health of said wearer of said garment.

25. The system of claim 24, where the first sensor comprises an ECG electrode.

26. The system of claim 24, where the second sensor comprises one of an air temperature sensor and an air humidity sensor.

27. The system of claim 24, wherein said at least one particular characteristic of said air comprises one of a change in temperature and a change of humidity of said air surrounding said garment.

28. The system of claim 24, wherein at least a portion of said at least one module is integrated into the garment.

29. The system of claim 24, wherein said at least one module comprises at least one module of a general purpose personal communication device.

30. The system of claim 24, wherein said at least one module comprises at least one module of a general purpose personal computer system.

31. The system of claim 24, wherein said at least one module comprises at least one module of a health-care enterprise computer system.

32. The garment of claim 1, wherein the garment comprises an air speed sensor, an air oxygen level sensor, a barometric pressure sensor, an altitude/elevation sensor, a precipitation sensor, a light sensor, or an orientation sensor.

33. The system of claim 8, wherein the garment comprises an air speed sensor, an air oxygen level sensor, a barometric pressure sensor, an altitude/elevation sensor, a precipitation sensor, a light sensor, or an orientation sensor.

34. The garment of claim 13, wherein the garment comprises an air speed sensor, an air oxygen level sensor, a barometric pressure sensor, an altitude/elevation sensor, a precipitation sensor, a light sensor, or an orientation sensor.

35. The system of claim 24, wherein the garment comprises an air speed sensor, an air oxygen level sensor, a barometric pressure sensor, an altitude/elevation sensor, a precipitation sensor, a light sensor, or an orientation sensor.

36. The garment of claim 1, wherein the processing of signals from said ECG sensors is initiated upon detection of a change of a signal from a sensor of at least one non-physiological characteristic by at least one threshold amount.

37. The garment of claim 1, wherein the processing of signals from said ECG sensors is initiated upon detection of a particular level of a non-physiological characteristic for a particular amount of time.

38. The garment of claim 1, wherein the processing of signals from said ECG sensors is initiated upon detection of a particular physical activity of the wearer of the garment.

39. The garment of claim 1, wherein the processing of signals from said ECG sensors is initiated upon detection that the wearer of the garment is at a particular physical location.

40. The system of claim 8, wherein the analysis of the plurality of signals from said plurality of ECG sensors is initiated upon detection of a change of a signal from a sensor of at least one non-physiological characteristic by at least one threshold amount.

41. The system of claim 8, wherein the analysis of the plurality of signals from said plurality of ECG sensors is initiated upon detection of a particular level of a non-physiological characteristic for a particular amount of time.

42. The system of claim 8, wherein the analysis of the plurality of signals from said plurality of ECG sensors is initiated upon detection of a particular physical activity of the wearer of the garment.

43. The system of claim 8, wherein the analysis of the plurality of signals from said plurality of ECG sensors is initiated upon detection that the wearer of the garment is at a particular physical location.

44. The system of claim 13, wherein the processing of signals from said first sensor is initiated upon detection of a change of a signal from a sensor of at least one non-physiological characteristic by at least one threshold amount.

45. The system of claim 13, wherein the processing of signals from said first sensor is initiated upon detection of a particular level of a non-physiological characteristic for a particular amount of time.

46. The system of claim 13, wherein the processing of signals from said first sensor is initiated upon detection of a particular physical activity of the wearer of the garment.

47. The system of claim 13, wherein the processing of signals from said first sensor is initiated upon detection that the wearer of the garment is at a particular physical location.

48. The system of claim 24, wherein the analysis of said first signal is initiated upon detection of a change of a signal from a sensor of at least one non-physiological characteristic by at least one threshold amount.

49. The system of claim 24, wherein the analysis of said first signal is initiated upon detection of a particular level of a non-physiological characteristic for a particular amount of time.

50. The system of claim 24, wherein the analysis of said first signal is initiated upon detection of a particular physical activity of the wearer of the garment.

51. The system of claim 24, wherein the analysis of said first signal is initiated upon detection that the wearer of the garment is at a particular physical location.

* * * * *